US009990208B2

(12) United States Patent
Sutton, II et al.

(10) Patent No.: US 9,990,208 B2
(45) Date of Patent: *Jun. 5, 2018

(54) SYSTEM AND METHOD FOR EXECUTION OF A SECURED ENVIRONMENT INITIALIZATION INSTRUCTION

(71) Applicant: Intel Corporation, Santa Clara, CA (US)

(72) Inventors: James A. Sutton, II, Portland, OR (US); David W. Grawrock, Aloha, OR (US)

(73) Assignee: Intel Corporation, Santa Clara, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/402,663

(22) Filed: Jan. 10, 2017

(65) Prior Publication Data

US 2017/0115993 A1    Apr. 27, 2017

Related U.S. Application Data

(63) Continuation of application No. 14/864,450, filed on Sep. 24, 2015, which is a continuation of application
(Continued)

(51) Int. Cl.
*G06F 9/44* (2018.01)
*G06F 12/14* (2006.01)
(Continued)

(52) U.S. Cl.
CPC ......... *G06F 9/4403* (2013.01); *G01N 23/223* (2013.01); *G01N 33/502* (2013.01);
(Continued)

(58) Field of Classification Search
CPC ...... G06F 9/4403; G06F 21/57; G06F 21/572; G06F 9/44505; G06F 12/0802;
(Continued)

(56) References Cited

U.S. PATENT DOCUMENTS 3,699,532 A  10/1972 Schaffer et al.
3,996,449 A  12/1976 Attanasio et al.
(Continued)

FOREIGN PATENT DOCUMENTS

CN  1042979 A  6/1990
CN  1065942 A  11/1992
(Continued)

OTHER PUBLICATIONS

Non-final Office Action from U.S. Appl. No. 12/413,655, dated Apr. 13, 2010, 15 pages.
(Continued)

*Primary Examiner* — Matthew Smithers
(74) *Attorney, Agent, or Firm* — Nicholson De Vos Webster & Elliott LLP

(57) ABSTRACT

A method and apparatus for initiating secure operations in a microprocessor system is described. In one embodiment, one initiating logical processor initiates the process by halting the execution of the other logical processors, and then loading initialization and secure virtual machine monitor software into memory. The initiating processor then loads the initialization software into secure memory for authentication and execution. The initialization software then authenticates and registers the secure virtual machine monitor software prior to secure system operations.

6 Claims, 8 Drawing Sheets

Related U.S. Application Data

No. 14/222,939, filed on Mar. 24, 2014, now Pat. No. 9,361,121, which is a continuation of application No. 13/835,997, filed on Mar. 15, 2013, now Pat. No. 9,043,594, which is a continuation of application No. 13/444,450, filed on Apr. 11, 2012, now Pat. No. 8,645,688, which is a continuation of application No. 12/455,844, filed on Jun. 8, 2009, now Pat. No. 8,185,734, which is a continuation of application No. 11/096,618, filed on Mar. 31, 2005, now Pat. No. 7,546,457, which is a continuation of application No. 10/112,169, filed on Mar. 29, 2002, now Pat. No. 7,069,442.

(51) Int. Cl.
| | | |
|---|---|---|
| *G06F 21/57* | (2013.01) | |
| *G06F 9/445* | (2018.01) | |
| *G01N 23/223* | (2006.01) | |
| *G01N 33/50* | (2006.01) | |
| *G01N 33/68* | (2006.01) | |
| *H04L 9/32* | (2006.01) | |
| *G06F 12/0802* | (2016.01) | |
| *G06F 13/42* | (2006.01) | |

(52) U.S. Cl.
CPC ..... *G01N 33/6872* (2013.01); *G06F 9/44505* (2013.01); *G06F 12/0802* (2013.01); *G06F 12/145* (2013.01); *G06F 12/1458* (2013.01); *G06F 13/4282* (2013.01); *G06F 21/57* (2013.01); *G06F 21/572* (2013.01); *H04L 9/32* (2013.01); *H04L 9/3247* (2013.01); *G01N 2223/076* (2013.01); *G06F 2212/1052* (2013.01); *G06F 2212/60* (2013.01); *G06F 2213/0026* (2013.01); *G06F 2221/033* (2013.01)

(58) Field of Classification Search
CPC ......... G06F 12/1458; G06F 2212/1052; G06F 2221/033; G06F 2212/60; G06F 12/145; G06F 13/4282; G06F 2213/0026; H04L 9/32; H04L 9/3247; G01N 33/502; G01N 33/6872; G01N 23/223; G01N 2223/076
See application file for complete search history.

(56) References Cited

U.S. PATENT DOCUMENTS

| | | | |
|---|---|---|---|
| 4,037,214 A | 7/1977 | Birney et al. | |
| 4,162,536 A | 7/1979 | Morley | |
| 4,207,609 A | 6/1980 | Luiz et al. | |
| 4,247,905 A | 1/1981 | Yoshida et al. | |
| 4,276,594 A | 6/1981 | Morley | |
| 4,278,837 A | 7/1981 | Best | |
| 4,307,214 A | 12/1981 | McDaniel et al. | |
| 4,307,447 A | 12/1981 | Provanzano et al. | |
| 4,319,233 A | 3/1982 | Matsuoka et al. | |
| 4,319,323 A | 3/1982 | Ermolovich et al. | |
| 4,347,565 A | 8/1982 | Kaneda et al. | |
| 4,366,537 A | 12/1982 | Heller et al. | |
| 4,403,283 A | 9/1983 | Myntti et al. | |
| 4,419,724 A | 12/1983 | Branigin et al. | |
| 4,430,709 A | 2/1984 | Schleupen | |
| 4,521,852 A | 6/1985 | Guttag | |
| 4,571,672 A | 2/1986 | Hatada et al. | |
| 4,759,064 A | 7/1988 | Chaum | |
| 4,795,893 A | 1/1989 | Ugon | |
| 4,802,084 A | 1/1989 | Ikegaya et al. | |
| 4,823,481 A | 4/1989 | Trotter | |
| 4,825,052 A | 4/1989 | Chemin et al. | |
| 4,907,270 A | 3/1990 | Hazard | |
| 4,907,272 A | 3/1990 | Hazard et al. | |
| 4,910,774 A | 3/1990 | Barakat | |
| 4,975,836 A | 12/1990 | Hirosawa et al. | |
| 5,007,082 A | 4/1991 | Cummins | |
| 5,020,911 A | 6/1991 | Gauert et al. | |
| 5,022,077 A | 6/1991 | Bealkowski et al. | |
| 5,075,842 A | 12/1991 | Lai | |
| 5,079,737 A | 1/1992 | Hackbarth | |
| 5,123,101 A | 6/1992 | Sindhu | |
| 5,187,802 A | 2/1993 | Inoue et al. | |
| 5,230,069 A | 7/1993 | Brelsford et al. | |
| 5,237,616 A | 8/1993 | Abraham et al. | |
| 5,255,379 A | 10/1993 | Melo | |
| 5,287,363 A | 2/1994 | Wolf et al. | |
| 5,293,424 A | 3/1994 | Holtey et al. | |
| 5,295,251 A | 3/1994 | Wakui et al. | |
| 5,317,705 A | 5/1994 | Gannon et al. | |
| 5,319,760 A | 6/1994 | Mason et al. | |
| 5,361,375 A | 11/1994 | Ogi | |
| 5,386,552 A | 1/1995 | Garney | |
| 5,396,614 A | 3/1995 | Khalidi et al. | |
| 5,421,006 A | 5/1995 | Jablon et al. | |
| 5,434,999 A | 7/1995 | Goire et al. | |
| 5,437,033 A | 7/1995 | Inoue et al. | |
| 5,442,645 A | 8/1995 | Ugon et al. | |
| 5,452,656 A | 9/1995 | Becher et al. | |
| 5,455,909 A | 10/1995 | Blomgren et al. | |
| 5,459,867 A | 10/1995 | Adams et al. | |
| 5,459,869 A | 10/1995 | Spilo | |
| 5,469,557 A | 11/1995 | Salt et al. | |
| 5,473,692 A | 12/1995 | Davis | |
| 5,479,509 A | 12/1995 | Ugon | |
| 5,504,814 A | 4/1996 | Miyahara | |
| 5,504,922 A | 4/1996 | Seki et al. | |
| 5,506,975 A | 4/1996 | Onodera | |
| 5,511,217 A | 4/1996 | Nakajima et al. | |
| 5,522,075 A | 5/1996 | Robinson et al. | |
| 5,528,231 A | 6/1996 | Patarin | |
| 5,533,126 A | 7/1996 | Hazard | |
| 5,555,385 A | 9/1996 | Osisek | |
| 5,555,414 A | 9/1996 | Hough et al. | |
| 5,560,013 A | 9/1996 | Scalzi et al. | |
| 5,564,040 A | 10/1996 | Kubala | |
| 5,566,323 A | 10/1996 | Ugon | |
| 5,568,552 A | 10/1996 | Davis | |
| 5,574,936 A | 11/1996 | Ryba et al. | |
| 5,582,717 A | 12/1996 | Di Santo | |
| 5,604,805 A | 2/1997 | Brands | |
| 5,606,617 A | 2/1997 | Brands | |
| 5,615,263 A | 3/1997 | Takahashi | |
| 5,628,022 A | 5/1997 | Ueno et al. | |
| 5,628,023 A | 5/1997 | Bryant et al. | |
| 5,633,929 A | 5/1997 | Kaliski, Jr. | |
| 5,657,445 A | 8/1997 | Pearce | |
| 5,668,971 A | 9/1997 | Neufeld | |
| 5,684,948 A | 11/1997 | Johnson et al. | |
| 5,706,469 A | 1/1998 | Kobayashi | |
| 5,717,903 A | 2/1998 | Bonola | |
| 5,720,609 A | 2/1998 | Pfefferle | |
| 5,721,222 A | 2/1998 | Bernstein et al. | |
| 5,729,760 A | 3/1998 | Poisner | |
| 5,737,604 A | 4/1998 | Miller et al. | |
| 5,737,760 A | 4/1998 | Grimmer, Jr. et al. | |
| 5,740,178 A | 4/1998 | Jacks et al. | |
| 5,752,046 A | 5/1998 | Oprescu et al. | |
| 5,757,919 A | 5/1998 | Herbert et al. | |
| 5,764,889 A | 6/1998 | Ault et al. | |
| 5,764,969 A | 6/1998 | Kahle et al. | |
| 5,796,835 A | 8/1998 | Saada | |
| 5,796,845 A | 8/1998 | Serikawa et al. | |
| 5,805,712 A | 9/1998 | Davis | |
| 5,809,546 A | 9/1998 | Greenstein et al. | |
| 5,825,875 A | 10/1998 | Ugon | |
| 5,825,880 A | 10/1998 | Sudia et al. | |
| 5,835,594 A | 11/1998 | Albrecht et al. | |
| 5,844,986 A | 12/1998 | Davis | |
| 5,852,717 A | 12/1998 | Bhide et al. | |
| 5,854,913 A | 12/1998 | Goetz et al. | |
| 5,867,577 A | 2/1999 | Patarin | |

(56) References Cited

U.S. PATENT DOCUMENTS

| | | | |
|---|---|---|---|
| 5,872,994 A | 2/1999 | Akiyama et al. |
| 5,889,947 A | 3/1999 | Starke |
| 5,890,189 A | 3/1999 | Nozue et al. |
| 5,892,944 A | 4/1999 | Fukumoto et al. |
| 5,900,606 A | 5/1999 | Rigal et al. |
| 5,901,225 A | 5/1999 | Ireton et al. |
| 5,903,752 A | 5/1999 | Dingwall et al. |
| 5,919,257 A | 7/1999 | Trostle |
| 5,935,242 A | 8/1999 | Madany et al. |
| 5,935,247 A | 8/1999 | Pai et al. |
| 5,935,249 A | 8/1999 | Stern et al. |
| 5,937,063 A | 8/1999 | Davis |
| 5,953,502 A | 9/1999 | Helbig, Sr. |
| 5,956,408 A | 9/1999 | Arnold |
| 5,970,147 A | 10/1999 | Davis |
| 5,978,475 A | 11/1999 | Schneier et al. |
| 5,978,481 A | 11/1999 | Ganesan et al. |
| 5,987,557 A | 11/1999 | Ebrahim |
| 5,987,604 A | 11/1999 | Edrich |
| 6,014,745 A | 1/2000 | Ashe |
| 6,035,374 A | 3/2000 | Panwar et al. |
| 6,035,380 A | 3/2000 | Shelton et al. |
| 6,044,478 A | 3/2000 | Green |
| 6,047,354 A | 4/2000 | Yoshioka et al. |
| 6,055,637 A | 4/2000 | Hudson et al. |
| 6,058,478 A | 5/2000 | Davis |
| 6,061,794 A | 5/2000 | Angelo et al. |
| 6,075,938 A | 6/2000 | Bugnion et al. |
| 6,076,160 A | 6/2000 | Wisor |
| 6,085,296 A | 7/2000 | Karkhanis et al. |
| 6,088,262 A | 7/2000 | Nasu |
| 6,092,095 A | 7/2000 | Maytal |
| 6,093,213 A | 7/2000 | Favor et al. |
| 6,101,584 A | 8/2000 | Satou et al. |
| 6,108,644 A | 8/2000 | Goldschlag et al. |
| 6,115,816 A | 9/2000 | Davis |
| 6,125,430 A | 9/2000 | Noel et al. |
| 6,131,166 A | 10/2000 | Wong-Insley |
| 6,148,379 A | 11/2000 | Schimmel |
| 6,158,546 A | 12/2000 | Hanson et al. |
| 6,173,417 B1 | 1/2001 | Merrill |
| 6,175,924 B1 | 1/2001 | Arnold |
| 6,175,925 B1 | 1/2001 | Nardone et al. |
| 6,178,509 B1 | 1/2001 | Nardone et al. |
| 6,182,089 B1 | 1/2001 | Ganapathy et al. |
| 6,188,257 B1 | 2/2001 | Buer |
| 6,192,455 B1 | 2/2001 | Bogin et al. |
| 6,199,152 B1 | 3/2001 | Kelly et al. |
| 6,205,550 B1 | 3/2001 | Nardone et al. |
| 6,212,635 B1 | 4/2001 | Reardon |
| 6,222,923 B1 | 4/2001 | Schwenk |
| 6,249,872 B1 | 6/2001 | Wildgrube et al. |
| 6,252,650 B1 | 6/2001 | Nakamura |
| 6,269,392 B1 | 7/2001 | Cotichini et al. |
| 6,272,533 B1 | 8/2001 | Browne |
| 6,272,637 B1 | 8/2001 | Little et al. |
| 6,275,933 B1 | 8/2001 | Fine et al. |
| 6,282,650 B1 | 8/2001 | Davis |
| 6,282,651 B1 | 8/2001 | Ashe |
| 6,282,657 B1 | 8/2001 | Kaplan et al. |
| 6,292,874 B1 | 9/2001 | Barnett |
| 6,301,646 B1 | 10/2001 | Hostetler |
| 6,308,270 B1 | 10/2001 | Guthery |
| 6,314,409 B2 | 11/2001 | Schneck et al. |
| 6,321,314 B1 | 11/2001 | Van Dyke |
| 6,327,646 B1 | 12/2001 | Sharma et al. |
| 6,327,652 B1 | 12/2001 | England et al. |
| 6,330,670 B1 | 12/2001 | England et al. |
| 6,339,815 B1 | 1/2002 | Feng et al. |
| 6,339,816 B1 | 1/2002 | Bausch |
| 6,356,989 B1 | 3/2002 | Hays et al. |
| 6,357,004 B1 | 3/2002 | Davis |
| 6,363,485 B1 | 3/2002 | Adams et al. |
| 6,374,286 B1 | 4/2002 | Gee et al. |
| 6,374,317 B1 | 4/2002 | Ajanovic et al. |
| 6,378,068 B1 | 4/2002 | Foster et al. |
| 6,378,072 B1 | 4/2002 | Collins et al. |
| 6,389,537 B1 | 5/2002 | Davis et al. |
| 6,397,242 B1 | 5/2002 | Devine et al. |
| 6,397,379 B1 | 5/2002 | Yates, Jr. et al. |
| 6,412,035 B1 | 6/2002 | Webber |
| 6,418,521 B1 | 7/2002 | Mathews et al. |
| 6,421,702 B1 | 7/2002 | Gulick |
| 6,435,416 B1 | 8/2002 | Slassi |
| 6,445,797 B1 | 9/2002 | McGough |
| 6,457,068 B1 | 9/2002 | Nayyar et al. |
| 6,463,535 B1 | 10/2002 | Drews |
| 6,463,537 B1 | 10/2002 | Tello |
| 6,499,123 B1 | 12/2002 | McFarland et al. |
| 6,505,279 B1 | 1/2003 | Phillips et al. |
| 6,507,904 B1 | 1/2003 | Ellison et al. |
| 6,510,508 B1 | 1/2003 | Zuraski, Jr. et al. |
| 6,529,909 B1 | 3/2003 | Bowman-Amuah |
| 6,535,988 B1 | 3/2003 | Poisner |
| 6,557,104 B2 | 4/2003 | Vu et al. |
| 6,560,627 B1 | 5/2003 | McDonald et al. |
| 6,604,187 B1 | 8/2003 | McGrath et al. |
| 6,609,199 B1 | 8/2003 | Detreville |
| 6,615,278 B1 | 9/2003 | Curtis |
| 6,633,963 B1 | 10/2003 | Ellison et al. |
| 6,633,981 B1 | 10/2003 | Davis |
| 6,651,171 B1 | 11/2003 | England et al. |
| 6,678,825 B1 | 1/2004 | Ellison et al. |
| 6,684,326 B1 | 1/2004 | Cromer et al. |
| 6,704,871 B1 * | 3/2004 | Kaplan ............... G06F 21/72 713/192 |
| 6,708,273 B1 * | 3/2004 | Ober ............... G06F 8/60 713/189 |
| 6,754,815 B1 | 6/2004 | Ellison et al. |
| 6,760,441 B1 | 7/2004 | Ellison et al. |
| 6,769,058 B1 | 7/2004 | Ellison et al. |
| 6,779,085 B2 | 8/2004 | Chauvel |
| 6,785,886 B1 | 8/2004 | Lim et al. |
| 6,795,905 B1 | 9/2004 | Ellison et al. |
| 6,938,164 B1 | 8/2005 | England et al. |
| 6,986,052 B1 * | 1/2006 | Mittal ............... G06F 12/1441 711/E12.097 |
| 7,024,555 B2 | 4/2006 | Kozuch et al. |
| 7,065,654 B1 * | 6/2006 | Gulick ............... G06F 21/85 713/164 |
| 7,069,442 B2 * | 6/2006 | Sutton, II ............... G06F 21/57 380/45 |
| 7,082,615 B1 * | 7/2006 | Ellison ............... G06F 9/468 380/44 |
| 7,085,935 B1 | 8/2006 | Ellison et al. |
| 7,103,529 B2 | 9/2006 | Zimmer |
| 7,111,086 B1 | 9/2006 | Ecoleston et al. |
| 7,124,170 B1 | 10/2006 | Sibert |
| 7,370,211 B2 * | 5/2008 | Rindborg ............... G06F 21/123 713/176 |
| 7,409,487 B1 | 8/2008 | Chen et al. |
| 7,546,457 B2 | 6/2009 | Sutton et al. |
| 7,552,254 B1 | 6/2009 | George et al. |
| 7,552,255 B1 | 6/2009 | George et al. |
| 7,793,111 B1 * | 9/2010 | McKeen ............... G06F 21/53 711/163 |
| 8,060,882 B2 * | 11/2011 | Gulick ............... G06F 9/4812 714/2 |
| 8,185,734 B2 * | 5/2012 | Sutton, II ............... G06F 21/57 713/164 |
| 8,187,534 B2 | 5/2012 | Mao |
| 8,386,788 B2 * | 2/2013 | Kozuch ............... G06F 21/57 713/176 |
| 8,645,688 B2 * | 2/2014 | Sutton, II ............... G06F 21/57 713/165 |
| 9,043,594 B2 * | 5/2015 | Sutton, II ............... G06F 21/57 713/164 |
| 9,361,121 B2 * | 6/2016 | Sutton, II ............... G06F 21/57 |
| 2001/0021969 A1 | 9/2001 | Burger et al. |
| 2001/0027511 A1 | 10/2001 | Wakabayashi et al. |
| 2001/0027527 A1 | 10/2001 | Khidekel et al. |
| 2001/0037450 A1 | 11/2001 | Metlitski et al. |
| 2002/0007456 A1 | 1/2002 | Peinado et al. |

(56) References Cited

U.S. PATENT DOCUMENTS

| | | | |
|---|---|---|---|
| 2002/0023032 A1 | 2/2002 | Pearson et al. | |
| 2002/0082824 A1 | 6/2002 | Neiger et al. | |
| 2002/0147916 A1 | 10/2002 | Strongin et al. | |
| 2002/0166061 A1 | 11/2002 | Falik et al. | |
| 2002/0169717 A1 | 11/2002 | Challener | |
| 2002/0184520 A1 | 12/2002 | Bush et al. | |
| 2003/0018892 A1 | 1/2003 | Tello | |
| 2003/0023867 A1* | 1/2003 | Thibadeau | G06F 21/805 713/165 |
| 2003/0074548 A1 | 4/2003 | Cromer et al. | |
| 2003/0074648 A1 | 4/2003 | Brassard et al. | |
| 2003/0084346 A1 | 5/2003 | Kozuch et al. | |
| 2003/0115453 A1 | 6/2003 | Grawrock | |
| 2003/0126442 A1 | 7/2003 | Glew et al. | |
| 2003/0126453 A1 | 7/2003 | Glew et al. | |
| 2003/0140238 A1* | 7/2003 | Turkboylari | G06F 21/575 713/193 |
| 2003/0159056 A1 | 8/2003 | Cromer et al. | |
| 2003/0188179 A1 | 10/2003 | Challener et al. | |
| 2003/0196085 A1 | 10/2003 | Lampson et al. | |
| 2003/0217250 A1 | 11/2003 | Bennett et al. | |
| 2004/0117539 A1 | 6/2004 | Bennett et al. | |
| 2004/0117593 A1 | 6/2004 | Uhlig et al. | |
| 2004/0162930 A1 | 8/2004 | Forin et al. | |
| 2007/0006230 A1 | 1/2007 | Neiger et al. | |
| 2016/0056960 A1* | 2/2016 | Sutton | G06F 21/57 713/189 |
| 2017/0132014 A1 | 5/2017 | Sutton, II et al. | |

FOREIGN PATENT DOCUMENTS

| | | |
|---|---|---|
| CN | 1147650 A | 4/1997 |
| CN | 1159630 A | 9/1997 |
| CN | 1185609 A | 6/1998 |
| CN | 1203394 A | 12/1998 |
| CN | 1042979 C | 4/1999 |
| CN | 2359735 Y | 1/2000 |
| CN | 1264078 A | 8/2000 |
| CN | 1307283 A | 8/2001 |
| CN | 1325511 A | 12/2001 |
| CN | 102841995 B | 1/2016 |
| DE | 4217444 A1 | 12/1992 |
| EP | 0473913 A2 | 3/1992 |
| EP | 0600112 A1 | 6/1994 |
| EP | 0892521 A2 | 1/1999 |
| EP | 0930567 A2 | 7/1999 |
| EP | 0961193 A2 | 12/1999 |
| EP | 0965902 A2 | 12/1999 |
| EP | 1030237 A1 | 8/2000 |
| EP | 1055989 A1 | 11/2000 |
| EP | 1056014 A1 | 11/2000 |
| EP | 1085396 A1 | 3/2001 |
| EP | 1146715 A1 | 10/2001 |
| EP | 1271277 A2 | 1/2003 |
| JP | H02503122 A | 9/1990 |
| JP | H06119250 A | 4/1994 |
| JP | H1098876 A | 4/1998 |
| JP | H10301773 A | 11/1998 |
| JP | H10333902 A | 12/1998 |
| JP | H11149385 A | 6/1999 |
| JP | 2000076139 A | 3/2000 |
| JP | 2001118034 A | 4/2001 |
| JP | 2001309350 A | 11/2001 |
| JP | 2001318797 A | 11/2001 |
| JP | 2001524229 A | 11/2001 |
| JP | 2002041306 A | 2/2002 |
| JP | 2002091939 A | 3/2002 |
| JP | 2004500666 A | 1/2004 |
| JP | 2011155064 A | 8/2011 |
| JP | 2013235612 A | 11/2013 |
| TW | 473913 B | 1/2002 |
| TW | 476913 B | 1/2002 |
| TW | 479194 B | 3/2002 |
| WO | 9524696 A2 | 9/1995 |
| WO | 9524696 A3 | 2/1996 |
| WO | 9729567 A1 | 8/1997 |
| WO | 9812620 A1 | 3/1998 |
| WO | 9834365 A1 | 8/1998 |
| WO | 9844402 A1 | 10/1998 |
| WO | 9905600 A2 | 2/1999 |
| WO | 9909482 A1 | 2/1999 |
| WO | 9918511 A1 | 4/1999 |
| WO | 9905600 A3 | 5/1999 |
| WO | 9957863 A1 | 11/1999 |
| WO | 9965579 A1 | 12/1999 |
| WO | 0021238 A1 | 4/2000 |
| WO | 0062232 A1 | 10/2000 |
| WO | 0113199 A1 | 2/2001 |
| WO | 0116772 A1 | 3/2001 |
| WO | 0127723 A1 | 4/2001 |
| WO | 0127821 A2 | 4/2001 |
| WO | 0163994 A2 | 8/2001 |
| WO | 0175564 A2 | 10/2001 |
| WO | 0175565 A2 | 10/2001 |
| WO | 0175595 A2 | 10/2001 |
| WO | 0198876 A2 | 12/2001 |
| WO | 0201794 A2 | 1/2002 |
| WO | 0203208 A2 | 1/2002 |
| WO | 0217555 A2 | 2/2002 |
| WO | 0163994 A3 | 4/2002 |
| WO | 0127821 A3 | 5/2002 |
| WO | 0175565 A3 | 6/2002 |
| WO | 0175595 A3 | 7/2002 |
| WO | 02060121 A1 | 8/2002 |
| WO | 0201794 A3 | 9/2002 |
| WO | 02086684 A2 | 10/2002 |
| WO | 0175564 A3 | 1/2003 |
| WO | 0198876 A3 | 1/2003 |
| WO | 0217555 A3 | 1/2003 |
| WO | 0203208 A3 | 3/2003 |
| WO | 03058412 A2 | 7/2003 |
| WO | 02086684 A3 | 10/2003 |
| WO | 03085497 A2 | 10/2003 |
| WO | 03058412 A3 | 11/2004 |
| WO | 03085497 A3 | 9/2009 |

OTHER PUBLICATIONS

Non-Final Office Action from U.S. Appl. No. 12/455,844, dated Aug. 25, 2010, 5 pages.
Non-Final Office Action from U.S. Appl. No. 12/483,519, dated Jul. 20, 2010, 17 pages.
Non-Final Office Action from U.S. Appl. No. 13/444,450, dated May 9, 2013, 56 pages.
Non-Final Office Action from U.S. Appl. No. 13/835,997, dated Jul. 3, 2013, 8 pages.
Non-Final Office Action from U.S. Appl. No. 14/222,939, dated Mar. 12, 2015, 16 pages.
Non-Final Office Action from U.S. Appl. No. 14/864,450, dated Aug. 24, 2017, 12 pages.
Non-Final Office Action from U.S. Appl. No. 15/402,661, dated May 19, 2017, 14 pages.
Notice of Allowance from U.S. Appl. No. 10/112,169, dated Jan. 6, 2005, 30 pages.
Notice of Allowance from U.S. Appl. No. 10/112,169, dated Nov. 28, 2005, 9 pages.
Notice of Allowance from U.S. Appl. No. 11/096,618, dated May 19, 2008, 7 pages.
Notice of Allowance from U.S. Appl. No. 12/455,844, dated Jan. 12, 2012, 39 pages.
Notice of Allowance from U.S. Appl. No. 12/455,844, dated Oct. 11, 2011, 5 pages.
Notice of Allowance from U.S. Appl. No. 13/444,450, dated Sep. 24, 2013, 12 pages.
Notice of Allowance from U.S. Appl. No. 13/835,997, dated Dec. 23, 2013, 19 pages.
Notice of Allowance from U.S. Appl. No. 14/222,939, dated Feb. 2, 2016, 12 pages.
Notice of Allowance from U.S. Appl. No. 14/864,450, dated Apr. 7, 2017, 14 pages.

(56) References Cited

OTHER PUBLICATIONS

Notice of Allowance from U.S. Appl. No. 14/864,450, dated Dec. 13, 2017, 5 pages.
Notice of Allowance from U.S. Appl. No. 14/864,450, dated Dec. 21, 2016, 8 pages.
Notice of Allowance from U.S. Appl. No. 15/402,661, dated Dec. 11, 2017, 5 pages.
Notice of Reason(s) for Rejection from foreign counterpart Japanese Patent Application No. 2016-162738, dated Oct. 3, 2017, 8 pages.
Notification of Reason for Refusal from foreign counterpart Korean Patent Application No. 1020047015567, dated Apr. 17, 2006, 4 pages.
Office Action and Search report from foreign counterpart Taiwanese Patent Application No. 098118881, dated Jul. 15, 2013, 7 Pages.
Office Action and Search report from foreign counterpart Taiwanese Patent Application No. 103100721, dated May 29, 2015, 6 pages.
Office Action from foreign counterpart Chinese Patent Application No. 201210159183.2, dated Nov. 9, 2015, 11 pages.
Office Action from foreign counterpart Japanese Patent Application No. 2003-582616, dated Jun. 17, 2008, 5 pages.
Office Action from foreign counterpart Japanese Patent Application No. 2003-582616, dated Oct. 26, 2010, 6 pages.
Office Action from foreign counterpart Japanese Patent Application No. 2008-236958, dated May 10, 2011, 4 pages.
Office Action from foreign counterpart Japanese Patent Application No. 2011-155064, dated Apr. 30, 2013, 14 pages.
Office Action from foreign counterpart Japanese Patent Application No. 2011-155064, dated Nov. 20, 2012, 13 pages.
Office Action from foreign counterpart Japanese Patent Application No. 2011-155064, dated Sep. 10, 2013, 11 pages.
Office Action from foreign counterpart Japanese Patent Application No. 2011-155064, dated Sep. 2, 2014, 15 pages.
Office Action from foreign counterpart Japanese Patent Application No. 2012-092142, dated Jul. 16, 2013, 3 pages.
Office Action from foreign counterpart Japanese Patent Application No. 2013-154700, dated Dec. 4, 2015, 6 pages.
Office Action from foreign counterpart Japanese Patent Application No. 2013-154700, dated Jul. 15, 2014, 8 pages.
Office Action from foreign counterpart Japanese Patent Application No. 2014-003431, dated Apr. 14, 2015, 4 pages.
Office Action from foreign counterpart Japanese Patent Application No. 2014-003431, dated Oct. 28, 2014, 16 pages.
Office Action from foreign counterpart Japanese Patent Application No. 2014-203765, dated Dec. 15, 2015, 8 pages.
Office Action from foreign counterpart Japanese Patent Application No. JP2016162738, dated Jan. 4, 2017, 6 pages.
Response to Final office action from U.S. Appl. No. 12/413,655, dated Oct. 11, 2010, 6 pages.
Response to Non-final office action from U.S. Appl. No. 12/413,655, dated Jul. 9, 2010, 8 pages.
Richt S., et al. In-Circuit-Emulator Wird 'Echtzeittauglich' 2087 Elektronik, vol. 40 (16), Aug. 6, 1991, pp. 100-103.
Robin, et al., "Analysis of the Intel Pentium's Ability to Support a Secure Virtual Machine Monitor," Proceedings of the 9th USENIX Security Symposium, vol. 9, Aug. 14-17, 2000, 16 pages.
Rosenblum, M. "Vmware's Virtual Platform: A Virtual Machine Monitor for Commodity PCs," Proceedings of the 11th Hotchips Conference, Aug. 1999, pp. 185-196.
RSA Security Inc., "Hardware Authenticators," available at www.rsasecurity.com/node.asp?id=1158, 2004, 2 pages.
RSA Security Inc., "Software Authenticators," available at: http://www.rsa.com/node.aspx?id=1313, 2004, pp. 1-2.
RSA Security Inc., "RSA SecurID Authenticators: The gold standard in two-factor user authentication," 2003, SID DS 0103, 2 pages.
Saez et al., "A Hardware Scheduler for Complex Real-Time Systems," Proceedings of the IEEE International Symposium on Industrial Electronics, Jul. 12-16, 1999, pp. 43-48.

Schneier, "Applied Cryptography: Protocols, Algorithms, and Source Code in C," 2nd Edition, Wiley, John & Sons, Inc., Oct. 1995, pp. 47-52, 56-65, 169-187.
Schneier B., "Applied Cryptography: Protocols, Algorithm, and Source Code in C", 2.sup.nd Edition, Wiley, John & Sons, Inc., ISBN 0471128457 (softcover printing), Nov. 1995, pp. 28-33, 176-177, 216-217, 461-473, 518-522.
Abandonment from U.S. Appl. No. 11/096,618, mailed Sep. 11, 2008, 1 page.
Abandonment from U.S. Appl. No. 13/835,997, mailed Aug. 22, 2014, 1 page.
Berg Cliff "How Do I Create a Signed Applet?" Dr. Don's Journal, vol. 22 (8), Aug. 1997, 9 pages.
Brands S., "Restrictive Blinding of SecretKey Certificates," CWI XP002201306, Springer Verlag, Amsterdam, 1995, 35 pages.
Chien, et al., "Safe and Protected Execution for the MORPH/AMRM Reconfigurable Processor," 7th Annual IEEE Symposium, FCCM '99 Proceedings, ISBN 0-7695-0375-6, Apr. 1, 1999, 13 pages.
Compaq Computer Corporation, Hewlett-Packard Company, IBM Corporation, Intel Corporation, Microsoft Corporation "Trusted Computing Platform Alliance (TCPA)" Main Specification Version1.1a Dec. 2001. 326 pgs.
Coulouris et al., "Distributed Systems, Concepts and Designs," Queen Mary and Westfield College University of London 2nd edition Addison-Wesley Publishing Ltd, 1994, pp. 422-424.
Crawford J., "Architecture of the Intel 80386," IEEE, Jan. 1986, pp. 155-160.
Davida et al. "Defending Systems Against Viruses through Cryptographic Authentication," IEEE, Jul. 1989, pp. 312-318.
Examination Report Under Section 18 (3) for foreign counterpart United Kingdom Application No. GB04220786, dated Jul. 27, 2005, 4 pages.
Examination Report Under Section 18 (3) for foreign counterpart United Kingdom Application No. GB0422078.6, dated Oct. 6, 2005, 3 pages.
Examiner's Decision of Refusal for foreign counterpart Japan Application No. 2013-154700, dated Oct. 28, 2014, 11 pages.
Fabry R.S., "Capability-Based Addressing," Communications of the ACM, vol. 17 (7), Jul. 1974, pp. 403-412.
Final Office Action from U.S. Appl. No. 12/413,655, dated Aug. 13, 2010, 12 pages.
Final Office Action from U.S. Appl. No. 12/455,844, dated Apr. 21, 2011, 15 pages.
Final Office Action from U.S. Appl. No. 14/222,939, dated Oct. 5, 2015, 49 pages.
Final Office Action from U.S. Appl. No. 15/402,661, dated Sep. 5, 2017, 5 pages.
First Office Action and Search Report from foreign counterpart China Patent Application No. 201510622256, dated Aug. 1, 2017, 12 pages.
First Office Action and Search report from foreign counterpart Chinese Patent Application No. 201310419555.5, dated Nov. 4, 2015, 11 pages.
First Office Action and Search report from foreign counterpart Chinese Patent Application No. 201210162765.6, dadted Sep. 2, 2014, 17 pages.
First Office Action from foreign counterpart Chinese Patent Application No. 03811454.2, dated Nov. 20, 2009, 11 pages.
First Office Action from foreign counterpart Chinese Patent Application No. 201010161984, dated Apr. 8, 2011, 8 pages.
First Office Action from foreign counterpart Chinese Patent Application No. 201110030876, dated Jan. 29, 2012, 19 pages.
First Office Action from foreign counterpart Chinese Patent Application No. 201210056872, dated May 30, 2014, 9 pages.
First Office Action from foreign counterpart Chinese Patent Application No. 201210159183, dated Sep. 16, 2014, 13 pages.
First Office Action from foreign counterpart Chinese Patent Application No. 201210159237, dated Oct. 31, 2014, 13 pages.
Fourth Office Action from foreign counterpart Chinese Patent Application No. 201010161984, dated Nov. 22, 2012, 7 pages.
Frieder, Dr. Gideon, "The Architecture and Operational Characteristics of the VMX Host Machine," IEEE, 1982, pp. 9-16.

(56) References Cited

OTHER PUBLICATIONS

Goldberg R., "Survey of Virtual Machine Research," IEEE Computer, vol. 7 (6), Jun. 1974, pp. 34-45.
Gong, et al., "Going Beyond the Sandbox: An Overview of the New Security Architecture in the Java Development Kit 1.2," USENIX, Symposium on Internet Technologies and Systems, Dec. 1997, 11 pages.
Gum, P.H., "System/370 Extended Architecture: Facilities for Virtual Machines," IBM, J. Res. Develop., vol. 27 (6), Nov. 1983, pp. 530-544.
Heinrich J., "MIPS R4000 Microprocessor User's Manual;" Memory Management, Apr. 1, 1993, MIPS, Mt. View, XP002184449, pp. 61-97.
Hewlettpackard Company, "Mobile Security Overview," Sep. 2002, 10 pages.
IBM Corporation, "IBM ThinkPad T30 Notebooks", IBM Product Specification, located at www-1.ibm.com/services/files/cisco_t30_spec_sheet_070202.pdf, pp. 1-6 (Jul. 2, 2002).
IBM, "Information Display Technique for a Terminate Stay Resident Program IBM Technical Disclosure Bulletin," TDB-ACC-No. NA9112156, Dec. 1, 1991, vol. 34 (7A), pp. 156-158.
Intel Corporation, "IA-64 System Abstraction Layer Specification," Intel Product Specification Order No. 245359-001, Jan. 2000, pp. 1-112.
Intel Corporation, "Intel 82802AB/82802AC Firmware Hub (FWH)," Intel Product Datasheet Document No. 290658-004, Nov. 2000, pp. 1-6 & 17-28.
Intel Corporation, "Intel IA-64 Architecture Software Developers Manual—vol. 2: IA-64 System Architecture," Intel Product Manual, Order No. 245318-001, Jan. 2000, pp. i, ii, 5.1-5.3, 11.1-11.8, 11.23-11.26.
Intel Corporation, "Intel386 DX Microprocessor 32-Bit CHMOS Microprocessor With Integrated Memory Management," Dec. 31, 1995, pp. 5-56.
Intel, "IA-32 Intel Architecture Software Developer's Manual Citation: vol. 3: System Programming Guide Miscellaneous Information," 2003, pp. 13-1 through 13-24.
International Search Report for Application No. PCT/US2003/08762, dated Aug. 12, 2003, 7 pages.
International Preliminary Examination Report for Application No. PCT/US03/08762, dated Jan. 24, 2005, 3 pages.
Karger P.A., et al., "A VMM Security Kernel for the VAX Architecture," Proceedings of the Symposium on Research in Security and Privacy, May 7, 1990, Boxborough, MA, XP010020182, ISBN: 0-8186-2060-9, pp. 2-19.
Kashiwagi, et al., "Design and Implementation of Dynamically Reconstructing System Software," IEEE, Aug. 1996, 11 pages.
Lawton, "Running Multiple Operating Systems Concurrently on an 1A32 PC Using Virtualization Techniques," Nov. 29, 1999, pp. 1-31, available at: http://www.floobydust.com/virtualization/lawton.1999.txt.
Luke et al. "Replacement Strategy for Aging Avionics Computers," IEEE Aerospace and Electronic Systems Magazine, Mar. 1999, vol. 14 (3), pp. 7-11.

Menezes, et al., "Handbook of Applied Cryptography," CRC Press LLC, 1997, ISBN: 0-8493-8523-7, 1996, pp. 403-405, 475, 506-515, 570.
Motorola Inc., "M68040 User's Manual," Motorola, 1990, 96 pages.
Nanba, et al., "VM/4: ACOS-4 Virtual Machine Architecture," Proceedings of the 12th annual international symposium on Computer architecture, IEEE, Jun. 1985, pp. 171-178.
Non-Final Office Action from U.S. Appl. No. 11/096,618, dated Sep. 10, 2007, 27 pages.
Second Office Action from foreign counterpart China Patent Application No. 201310419555.5, dated Apr. 22, 2016, 7 pages.
Second Office Action from foreign counterpart Chinese Patent Application No. 03811454.2, dated Jul. 19, 2010, 5 pages. (English translation only available).
Second Office Action from foreign counterpart Chinese Patent Application No. 201010161984, dated Dec. 16, 2011, 17 pages.
Second Office Action from foreign counterpart Chinese Patent Application No. 201110030876, dated Jul. 17, 2012, 9 pages.
Second Office Action from foreign counterpart Chinese Patent Application No. 201210056872, dated Jan. 19, 2015, 12 pages.
Second Office Action from foreign counterpart Chinese Patent Application No. 201210159183, dated May 13, 2015, 10 pages.
Second Office Action from foreign counterpart Chinese Patent Application No. 201210159237, dated Jun. 10, 2015, 13 pages.
Second Office Action from foreign counterpart Chinese Patent Application No. 201210162765, dated Apr. 29, 2015, 8 pages.
Sherwood, et al., "Patchable Instruction ROM Architecture," CASES'01, Nov. 16-17, 2001, pp. 24-33.
Sugerman et al., "Virtualization of I/O Device in Host-Cooperative VMM," VMware Workstation, UNIX Magazine, ASCII, Jan. 1, 2002, pp. 158-175.
Sugerman et al., "Virtualizing I/O Devices on VMware Workstation's Hosted Virtual Machine Monitor," Proceedings of the 2001 USENIX Annual Technical Conference, USENIX Association, Jun. 25-30, 2001, 15 pages.
Third Office Action from foreign counterpart Chinese Patent Application No. 201010161984, dated Jul. 11, 2012, 8 pages.
Third Office Action from foreign counterpart Chinese Patent Application No. 201110030876, dated Nov. 29, 2012, 10 pages.
Third Office Action from foreign counterpart Chinese Patent Application No. 201210056872, dated Aug. 12, 2015, 15 pages.
Tivoli Tme 10 Security Management TACF Manual, IBM Japan, Dec. 31, 1998, First edition, pp. 3-121.
"Trusted Computing Platform Alliance (TCPA)," Main Specification Version 1.1b, Feb. 22, 2002, pp. 2-15.
Trusted Computing Platform Alliance (TCPA) Main Specification Version 1.1b, Trusted Computing Group, Feb. 22, 2002, downloaded from http://www.trustedcomputinggroup.org/files/resource_files/64795356-1D09-3519-ADAB12F595B5FCDF/TCPAMainTCGArchitecturev1_1b.pdf on Oct. 21, 2014, 332 pages.
Notice on Grant of Patent Right for Invention for Application No. 201510622256.0, dated Feb. 28, 2018, 4 pages.
Office Action and Search Report from foreign counterpart Chinese Patent Application No. 201510995651.3, dated Jan. 2, 2018, 24 pages.

* cited by examiner

SYSTEM AND METHOD FOR EXECUTION OF A SECURED ENVIRONMENT INITIALIZATION INSTRUCTION

FIELD

The present invention relates generally to microprocessor systems, and more specifically to microprocessor systems that may operate in a trusted or secured environment.

BACKGROUND

The increasing number of financial and personal transactions being performed on local or remote microcomputers has given impetus for the establishment of "trusted" or "secured" microprocessor environments. The problem these environments try to solve is that of loss of privacy, or data being corrupted or abused. Users do not want their private data made public. They also do not want their data altered or used in inappropriate transactions. Examples of these include unintentional release of medical records or electronic theft of funds from an on-line bank or other depository. Similarly, content providers seek to protect digital content (for example, music, other audio, video, or other types of data in general) from being copied without authorization.

Existing trusted systems may utilize a complete closed set of trusted software. This method is relatively simple to implement, but has the disadvantage of not allowing the simultaneous use of common, commercially available operating system and application software. This disadvantage limits the acceptance of such a trusted system.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The following description describes techniques for initiating a trusted or secured environment in a microprocessor system. In the following description, numerous specific details such as logic implementations, software module allocation, encryption techniques, bus signaling techniques, and details of operation are set forth in order to provide a more thorough understanding of the present invention. It will be appreciated, however, by one skilled in the art that the invention may be practiced without such specific details. In other instances, control structures, gate level circuits and full software instruction sequences have not been shown in detail in order not to obscure the invention. Those of ordinary skill in the art, with the included descriptions, will be able to implement appropriate functionality without undue experimentation. The invention is disclosed in the form of a microprocessor system. However, the invention may be practiced in other forms of processor such as a digital signal processor, a minicomputer, or a mainframe computer.

Figure 1:
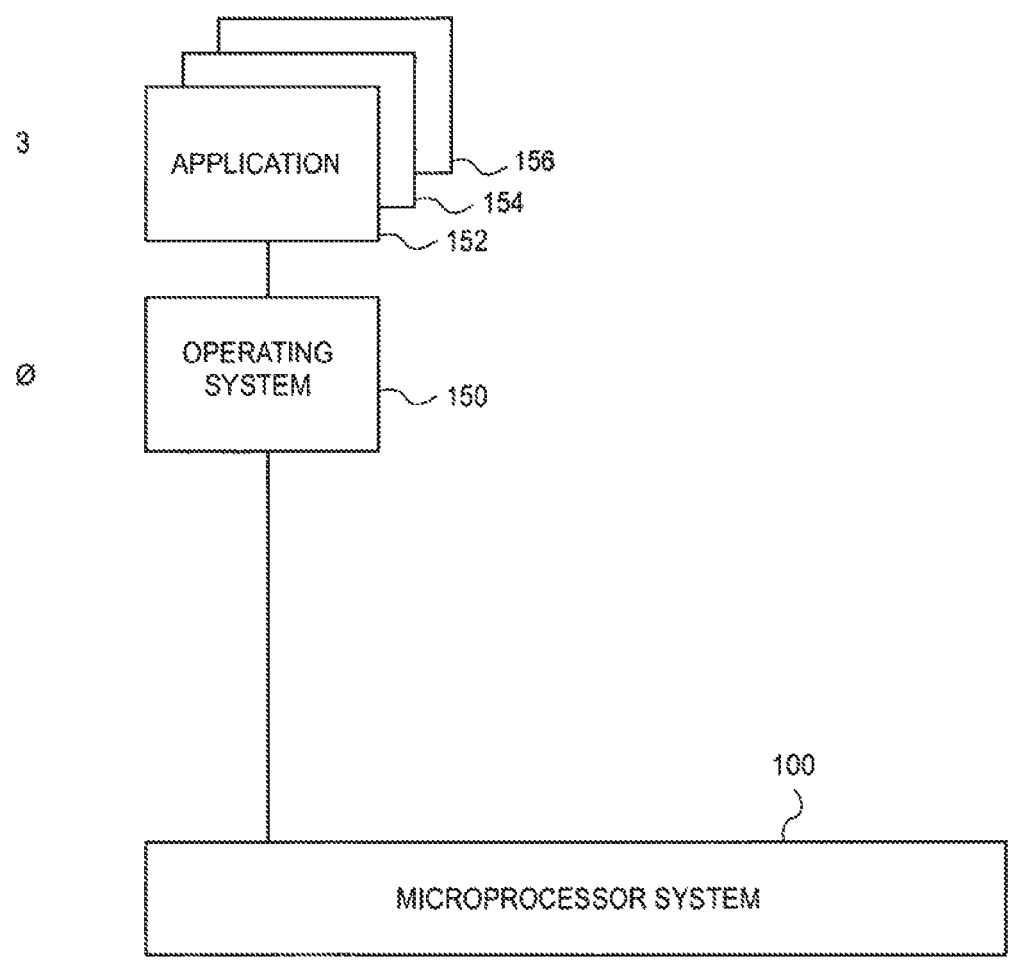
FIG. 1 is a diagram of an exemplary software environment executing in a microprocessor system.

Referring now to FIG. 1, a diagram of an exemplary software environment executing in a microprocessor system is shown. The software shown in FIG. 1 is not trusted (untrusted). When operating in a high privilege level, the size and constant updating of the operating system 150 make it very difficult to perform any trust analysis in a timely manner. Much of the operating system sits within privilege ring zero (0), the highest level of privilege. The applications 152, 154, and 156 have much reduced privilege and typically reside within privilege ring three (3). The existence of the differing privilege rings and the separation of the operating system 150 and applications 152, 154 and 156 into these differing privileged rings would appear to allow operating of the software of FIG. 1 in a trusted mode, based on making a decision to trust the facilities provided by the operating system 150. However, in practice making such a trust decision is often impractical. Factors that contribute to this problem include the size (number of lines of code) of the operating system 150, the fact that the operating system 150 may be the recipient of numerous updates (new code modules and patches) and the fact that the operating system 150 may also contain code modules such as device drivers supplied by parties other than the operating system developer. Operating system 150 may be a common one such as Microsoft® Windows®, Linux, or Solaris®, or may be any other appropriate known or otherwise available operating system. The particular types or names of applications or operating systems run or running are not critical.

Figure 2:
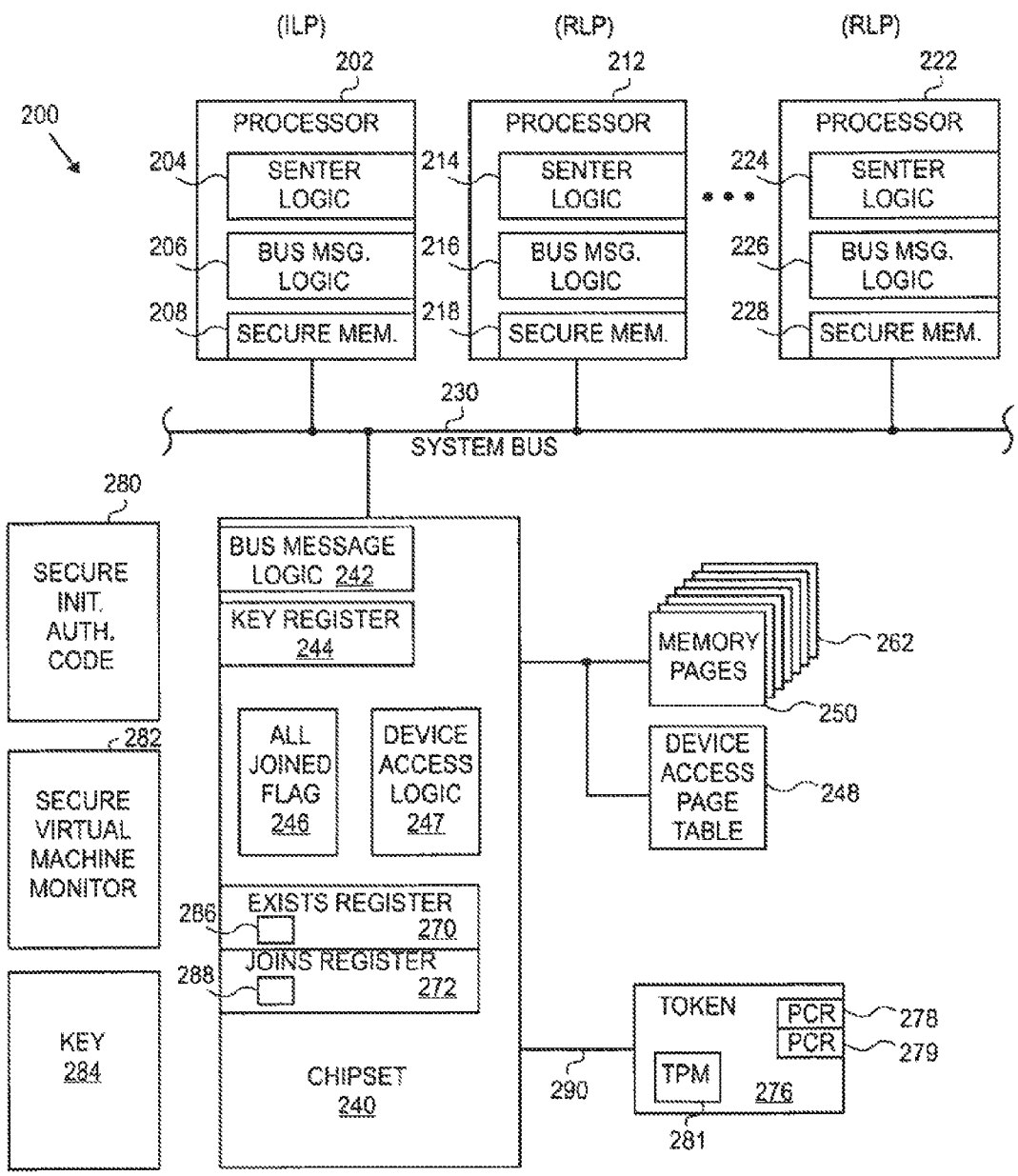
FIG. 2 is a diagram of certain exemplary trusted or secured software modules and exemplary system environment, according to one embodiment of the present invention.

Referring now to FIG. 2, a diagram of certain exemplary trusted or secured software modules and exemplary system environment 200 is shown, according to one embodiment of the present invention. In the FIG. 2 embodiment, processor 202, processor 212, processor 222, and optional other processors (not shown) are shown as separate hardware entities. In other embodiments, the number of processors may differ, as may the boundary of various components and functional units. In some embodiments the processors may be replaced by separate hardware execution threads or "logical processors" running on one or more physical processors.

Processors 202, 212, 222 may contain certain special circuits or logic elements to support secure or trusted operations. For example, processor 202 may contain secure enter (SENTER) logic 204 to support the execution of special SENTER instructions that may initiate trusted operations. Processor 202 may also contain bus message logic 206 to support special bus messages on system bus 230 in support of special SENTER operations. In alternate embodiments, memory control functions of chipset 240 may be allocated to circuits within the processors, and for multiple processors may be included on a single die. In these embodiments, special bus messages may also be sent on busses internal to the processors. The use of special bus messages may increase the security or trustability of the system for several reasons. Circuit elements such as processors 202, 212, and 222 or chipset 240 may only issue or respond to such messages if they contain the appropriate logic elements of embodiments of the present disclosure. Therefore successful exchange of the special bus messages may help ensure proper system configuration. Special bus messages may also permit activities that should normally be prohibited, such as resetting a platform configuration register 278. The ability of potentially hostile untrusted code to spy on certain bus transactions may be curtailed by allowing special bus messages to be issued only in response to special security instructions.

Additionally, processor 202 may contain secure memory 208 to support secure initialization operations. In one embodiment secure memory 208 may be an internal cache of processor 202, perhaps operating in a special mode. In alternate embodiments secure memory 208 may be special memory. Other processors such as processor 212 and processor 222 may also include SENTER logic 214, 224, bus message logic 216, 226, and secure memory 218, 228.

A "chipset" may be defined as a group of circuits and logic that support memory and input/output (I/O) operations for a connected processor or processors. Individual elements of a chipset may be grouped together on a single chip, a pair of chips, or dispersed among multiple chips, including processors. In the FIG. 2 embodiment, chipset 240 may include circuitry and logic to support memory and I/O operations to support processors 202, 212, and 222. In one embodiment, chipset 240 may interface with a number of memory pages 250 through 262 and a device-access page table 248 containing control information indicating whether non-processor devices may access the memory pages 250 through 262. Chipset 240 may include device-access logic 247 that may permit or deny direct memory access (DMA) from I/O devices to selected portions of the memory pages 250 through 262. In some embodiment the device access logic 247 may contain all relevant information required to permit or deny such accesses. In other embodiments, the device access logic 247 may access such information held in the device access page table 248. The actual number of memory pages is not important and will change depending upon system requirements. In other embodiments the memory access functions may be external to chipset 240. The functions of chipset 240 may further be allocated among one or more physical devices in alternate embodiments.

Chipset 240 may additionally include its own bus message logic 242 to support special bus messages on system bus 230 in support of special SENTER operations. Some of these special bus messages may include transferring the contents of a key register 244 to a processor 202, 212, or 222, or permitting a special ALL_JOINED flag 274 to be examined by a processor 202, 212, or 222. Additional features of the bus message logic 242 may be to register bus activity by processors in an "EXISTS" register 272 and store certain special bus message activity by processors in a "JOINS" register 272. Equality of contents of EXISTS register 272 and JOINS register 272 may be used to set the special ALL_JOINED flag 274 to indicate all processors in the system are participating in the secure enter process.

Chipset 240 may support standard I/O operations on I/O busses such as peripheral component interconnect (PCI), accelerated graphics port (AGP), universal serial bus (USB), low pin count (LPC) bus, or any other kind of I/O bus (not shown). An interface 290 may be used to connect chipset 240 with token 276, containing one or more platform configuration registers (PCR) 278, 279. In one embodiment, interface 290 may be the LPC bus (Low Pin Count (LPC) Interface Specification, Intel Corporation, rev. 1.0, 29 Dec. 1997) modified with the addition of certain security enhancements. One example of such a security enhancement would be a locality confirming message, utilizing a previously-reserved message header and address information targeting a platform configuration register (PCR) 278 within token 276. In one embodiment, token 276 may contain special security features, and in one embodiment may include the trusted platform module (TPM) 281 disclosed in the Trusted Computing Platform Alliance (TCPA) Main Specification, version 1.1a, 1 Dec. 2001, issued by the TCPA (available at the time of filing of the present application at www.trustedpc.com).

Two software components identified in system environment 200 are a Secure Virtual Machine Monitor (SVMM) 282 module and a Secure Initialization Authenticated Code (SINIT-AC) 280 module. The SVMM 282 module may be stored on a system disk or other mass storage, and moved or copied to other locations as necessary. In one embodiment, prior to beginning the secure launch process SVMM 282 may be moved or copied to one or more memory pages 250 through 262. Following the secure enter process, a virtual machine environment may be created in which the SVMM 282 may operate as the most privileged code within the system, and may be used to permit or deny direct access to certain system resources by the operating system or applications within the created virtual machines.

Some of the actions required by the secure enter process may be beyond the scope of simple hardware implementations, and may instead advantageously use a software module whose execution can be implicitly trusted. In one embodiment, these actions may be performed by Secure Initialization (SINIT) code. Three exemplary actions are identified here, but these actions should not be taken to be limiting. One action may require that various controls representing critical portions of the system configuration be tested to ensure that the configuration supports the correct instantiation of the secure environment. In one embodiment, one required test may be that the memory controller configuration provided by chipset 240 does not permit two or more different system bus addresses to touch the same location within memory pages 250 through 262. A second action may be to configure the device-access page table 248 and device-access logic 247 to protect those memory pages used by the memory-resident copy of SVMM 282 from interference by non-processor devices. A third action may be to calculate and register the SVMM 282 module's identity and transfer system control to it. Here "register" means placing a trust measurement of SVMM 282 into a register, for example into PCR 278 or into PCR 279. When this last action is taken, the trustworthiness of the SVMM 282 may be inspected by a potential system user.

The SINIT code may be produced by the manufacturer of the processors or of the chipsets. For this reason, the SINIT code may be trusted to aid in the secure launch of chipset 240. In order to distribute the SINIT code, in one embodiment a well-known cryptographic hash is made of the entire SINIT code, producing a value known as a "digest". One embodiment produces a 160-bit value for the digest. The digest may then be encrypted by a private key, held in one embodiment by the manufacturer of the processor, to form a digital signature. When the SINIT code is bundled with the corresponding digital signature, the combination may be referred to as SINIT authenticated code (SINIT-AC) 280. Copies of the SINIT-AC 280 may be later validated as discussed below.

The SINIT-AC 280 may be stored on system disk or other mass storage or in a fixed media, and moved or copied to other locations as necessary. In one embodiment, prior to beginning the secure launch process SINIT-AC 280 may be moved or copied into memory pages 250-262 to form a memory-resident copy of SINIT-AC.

Any logical processor may initiate the secure launch process, and may then be referred to as the initiating logical processor (ILP). In the present example processor 202 becomes the ILP, although any of the processors on system bus 230 could become the ILP. Neither memory-resident copy of SINIT-AC 280 nor memory-resident copy of SVMM 282 may be considered trustworthy at this time since, among other reasons, the other processors or the DMA devices may overwrite memory pages 250-262.

The ILP (processor 202) then executes a special instruction. This special instruction may be referred to as a secured enter (SENTER) instruction, and may be supported by SENTER logic 204. Execution of the SENTER instruction may cause the ILP (processor 202) to issue special bus messages on system bus 230, and then wait considerable time intervals for subsequent system actions. After execution of SENTER begins, one of these special bus messages, SENTER BUS MESSAGE, is broadcast on system bus 230. Those logical processors other than the ILP, which may be referred to as responding logical processors (RLPs), respond to the SENTER BUS MESSAGE with an internal non-maskable event. In the present example, the RLPs include processor 212 and processor 222. The RLPs must each terminate current operations, send a RLP acknowledge (ACK) special bus message on system bus 230, and then enter a wait state. It should be noted that the ILP also sends its own ACK message over system bus 230.

The chipset 240 may contain a pair of registers, "EXISTS" register 270 and "JOINS" register 272. These registers may be used to verify that the ILP and all of the RLPs are responding properly to the SENTER BUS MESSAGE. In one embodiment, chipset 240 may keep track of all operational logical processors in the system by writing a "1" into the corresponding bit of the EXISTS register 270 on any system bus transaction made by that logical processor. In this embodiment, each transaction on system bus 230 must contain an identification field containing the logical processor identifier. In one embodiment, this consists of a physical processor identifier and an indentifier for the hardware execution thread within each physical processor. For example, if a thread executing on processor 222 caused any bus transactions on system bus 230, chipset 240 would see this logical processor identifier within the transaction and write a "1" into the corresponding location 286 within EXISTS register 270. During the secure launch process, when that same thread on processor 222 sends its ACK message on system bus 230, the chipset 240 would also see this and could write a "1" into the corresponding location 288 in the JOINS register 272. (In the FIG. 2 example, each physical processor is shown with only a single thread executing for clarity. In alternate embodiments the physical processors may support multiple threads, and thereby multiple logical processors.) When the contents of the JOINS register 272 matches the contents of the EXISTS register 270, then chipset 240 can set an ALL_JOINED flag 246 indicating that all processors have properly responded to the SENTER BUS MESSAGE.

In another embodiment, EXISTS register 270 and JOINS register 272 may continue to aid security subsequent to the setting of the ALL_JOINED flag 246. During the time subsequent to the setting of the ALL_JOINED flag 246 until the end of trusted or secure operations, chipset 240 may continue to monitor and compare bus cycles_against the JOINS register 272. During this period, if chipset 240 ever sees a bus transaction from a logical processor that is not currently identified in JOINS register 272, then chipset 240 may presume that this logical processor has somehow "appeared" late. This would imply that such a logical processor did not participate in the secure launch process, and therefore could represent an attacker (security threat). In such circumstances, chipset 240 may respond appropriately to keep this attacker out of the secured environment. In one embodiment, chipset 240 may force a system reset in such circumstances. In a second embodiment, similar detection of a "late" processor may be achieved by each logical processor asserting a special reserved signal on the system bus on every transaction following the assertion of the ACK bus message. In this embodiment, following the setting of the ALL_JOINED flag 246 if the chipset 240 observes a bus transaction initiated by a processor without the special signal asserted, then chipset 240 may again presume that this logical processor has somehow appeared "late", and may represent an attacker.

After issuing the SENTER BUS MESSAGE, the ILP (processor 202) polls the ALL_JOINED flag 246 to see when and if all processors have properly responded with their ACKs. If the flag 246 is never set, several implementations are possible. A watchdog timer in the ILP or chipset or elsewhere may cause a system reset. Alternatively, the system may hang requiring operator reset. In either case the assertion of a secure environment is protected (in that the secure launch process does not complete unless all processors participate), although the system may not continue to function. In normal operations, after a short time the ALL_JOINED flag 246 is set, and the ILP may be assured that all other logical processors have entered a wait state.

When the ALL_JOINED flag 246 is set, the ILP (processor 202) may move both a copy of SINIT-AC 280 and key 284 into secure memory 208 for the purpose of authenticating and subsequently executing the SINIT code included in SINIT-AC 280. In one embodiment, this secure memory 208 may be an internal cache of the ILP (processor 202), perhaps operating in a special mode. Key 284 represents the public key corresponding to the private key used to encrypt the digital signature included in the SINIT-AC 280 module, and is used to verify the digital signature and thereby authenticate the SINIT code. In one embodiment, key 284 may already be stored in the processor, perhaps as part of the SENTER logic 204. In another embodiment, key 284 may be stored in a read-only key register 244 of chipset 240, which is read by the ILP. In yet another embodiment, either the processor or the chipset's key register 244 may actually hold a cryptographic digest of key 284, where key 284 itself is included in the SINIT-AC 280 module. In this last embodiment, the ILP reads the digest from key register 244, calculates an equivalent cryptographic hash over the key 284 embedded in SINIT-AC 280, and compares the two digests to ensure the supplied key 284 is indeed trusted.

A copy of SINIT-AC and a copy of a public key may then exist within secure memory 208. The ILP may now validate the copy of SINIT-AC by decrypting the digital signature included in the copy of the SINIT-AC using the copy of a public key. This decryption produces an original copy of a cryptographic hash's digest. If a newly-calculated digest matches this original digest then the copy of SINIT-AC and its included SINIT code may be considered trustable.

The ILP may now issue another special bus message, SENTER CONTINUE MESSAGE, via system bus 230 signaling the waiting RLP's (processor 212, processor 222) and chipset 240 that secured operations are going to be initiated. The ILP may now register the unique identity of the SINIT-AC module by writing the SINIT-AC module's cryptographic digest value to a platform configuration register 272 in the security token 276, as outlined below. The ILP's execution of its SENTER instruction may now terminate by transferring execution control to the trusted copy of the SINIT code held within the ILP's secure memory 208. The trusted SINIT code may then perform its system test and configuration actions and may register the memory-resident copy of SVMM, in accordance with the definition of "register" above.

Registration of the memory-resident copy of SVMM may be performed in several manners. In one embodiment, the SENTER instruction running on the ILP writes the calculated digest of SINIT-AC into PCR 278 within the security token 276. Subsequently, the trusted SINIT code may write the calculated digest of the memory-resident SVMM to the same PCR 278 or another PCR 279 within the security token 276. If the SVMM digest is written to the same PCR 278, the security token 276 hashes the original contents (SINIT digest) with the new value (SVMM digest) and writes the result back into the PCR 278. In embodiments where the first (initializing) write to PCR 278 is limited to the SENTER instruction, the resulting digest may be used as a root of trust for the system.

Once the trusted SINIT code has completed its execution, and has registered the identity of the SVMM in a PCR, the SINIT code may transfer ILP execution control to the SVMM. In a typical embodiment, the first SVMM instructions executed by the ILP may represent a self-initialization routine for the SVMM. The ILP may in one embodiment issue individual RLP JOIN MESSAGE special bus messages to each RLP, causing each of the RLPs to join in operations under the supervision of the now-executing copy of SVMM. From this point onwards, the overall system is operating in trusted mode as outlined in the discussion of FIG. 3 below.

Figure 3:
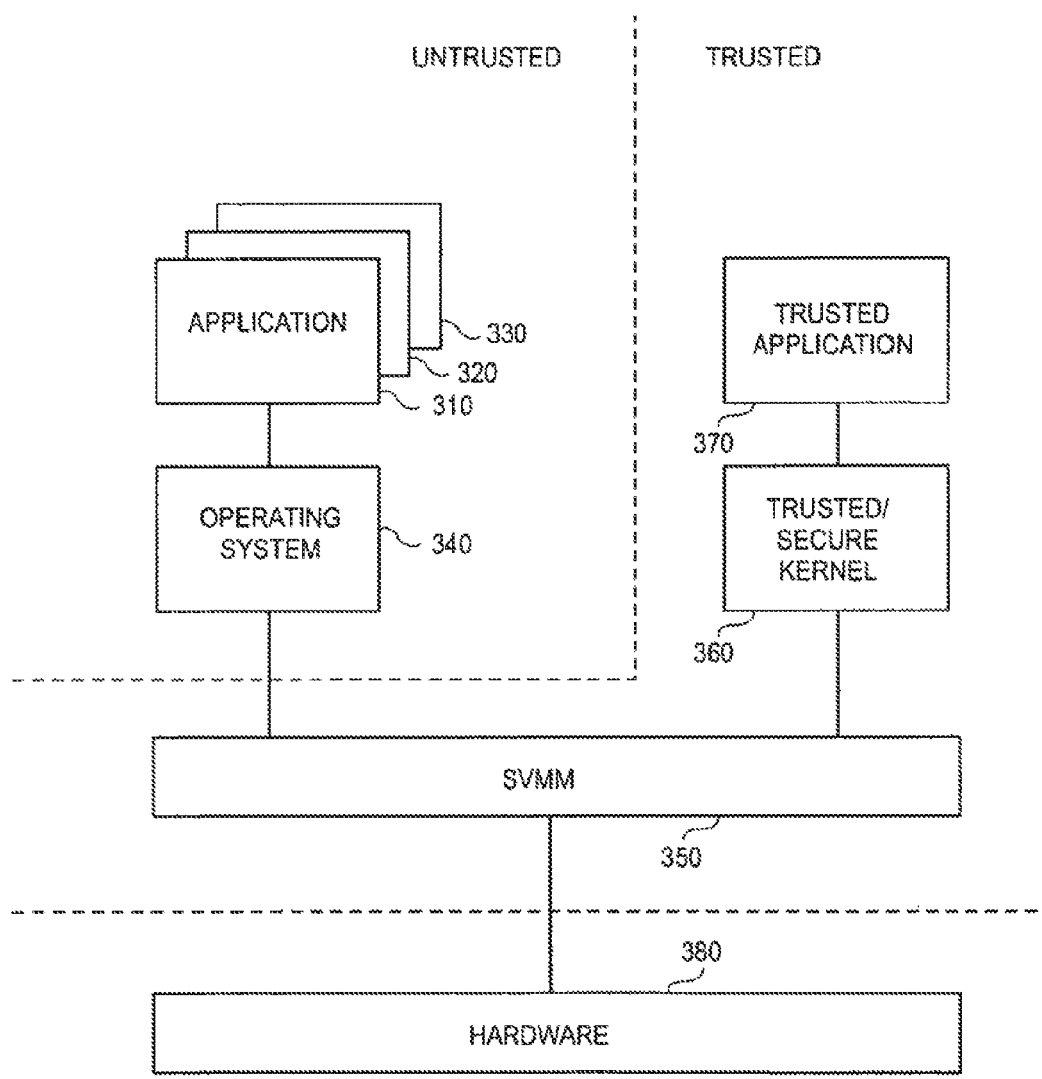
FIG. 3 is a diagram of an exemplary trusted or secured software environment, according to one embodiment of the present invention.

Referring now to FIG. 3, a diagram of an exemplary trusted or secured software environment is shown, according to one embodiment of the present invention. In the FIG. 3 embodiment, trusted and untrusted software may be loaded simultaneously and may execute simultaneously on a single computer system. A SVMM 350 selectively permits or prevents direct access to hardware resources 380 from one or more untrusted operating systems 340 and untrusted applications 310 through 330. In this context, "untrusted" does not necessarily mean that the operating system or applications are deliberately misbehaving, but that the size and variety of interacting code makes it impractical to reliably assert that the software is behaving as desired, and that there are no viruses or other foreign code interfering with its execution. In a typical embodiment, the untrusted code might consist of the normal operating system and applications found on today's personal computers.

SVMM 350 also selectively permits or prevents direct access to hardware resources 380 from one or more trusted or secure kernels 360 and one or more trusted applications 370. Such a trusted or secure kernel 360 and trusted applications 370 may be limited in size and functionality to aid in the ability to perform trust analysis upon it. The trusted application 370 may be any software code, program, routine, or set of routines which is executable in a secure environment. Thus, the trusted application 370 may be a variety of applications, or code sequences, or may be a relatively small application such as a Java applet.

Instructions or operations normally performed by operating system 340 or kernel 360 that could alter system resource protections or privileges may be trapped by SVMM 350, and selectively permitted, partially permitted, or rejected. As an example, in a typical embodiment, instructions that change the processor's page table that would normally be performed by operating system 340 or kernel 360 would instead be trapped by SVMM 350, which would ensure that the request was not attempting to change page privileges outside the domain of its virtual machine.

Figure 4A:
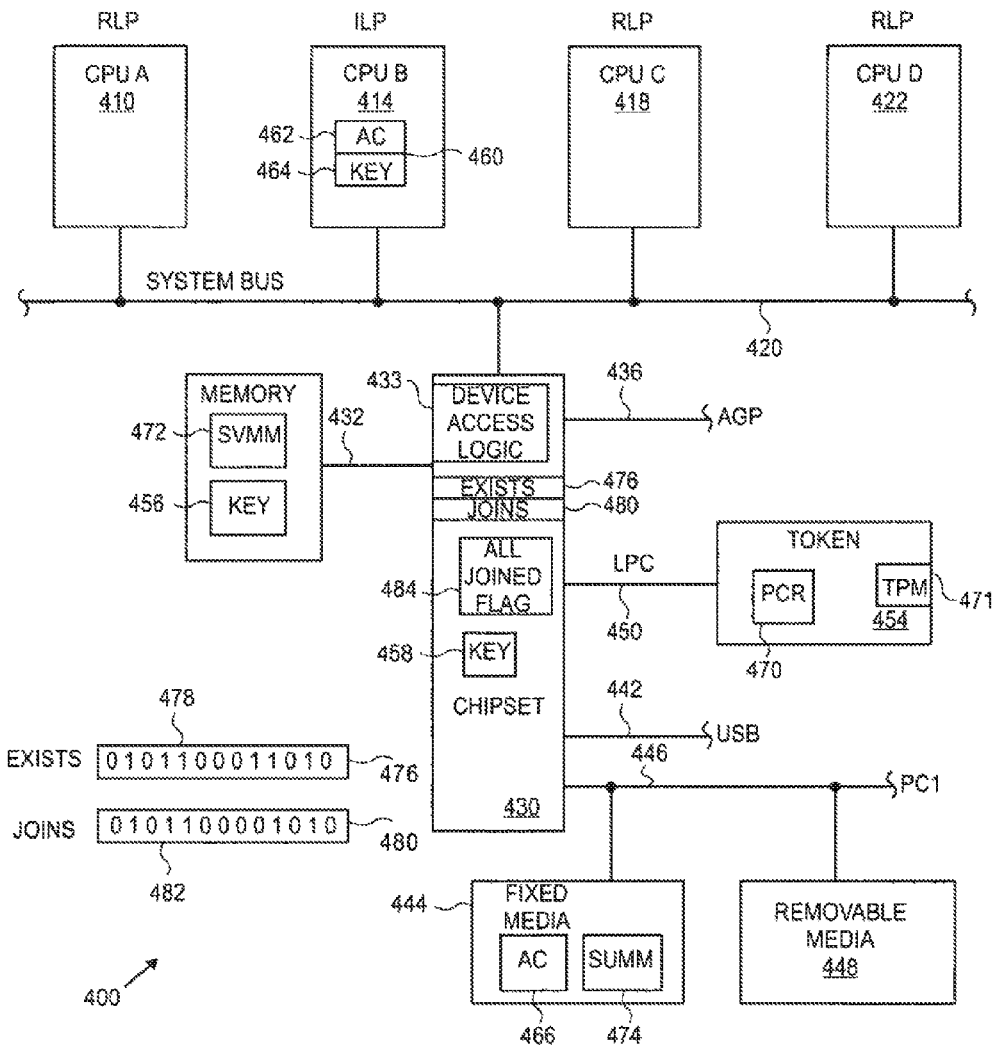
FIG. 4A is a schematic diagram of an exemplary microprocessor system adapted to support the secured software environment of FIG. 3, according to one embodiment of the present invention.

Referring now to FIG. 4A, one embodiment of a microprocessor system 400 adapted to support the secured software environment of FIG. 3 is shown. CPU A 410, CPU B 414, CPU C 418, and CPU D 422 may be configured with additional microcode or logic circuitry to support the execution of special instructions. In one embodiment, this additional microcode or logic circuitry may be the SENTER logic 204 of FIG. 2. These special instructions may support the issuance of special bus messages on system bus 420 that may enable the proper synchronization of the processors while launching the secure environment. In one embodiment, the issuance of special bus messages may be supported by circuitry such as the bus message logic 206 of FIG. 2. Similarly chipset 430 may be similar to chipset 240 and may support the above-mentioned special cycles on system bus 420. The number of physical processors may vary upon the implementation of a particular embodiment. In one embodiment, the processors may be Intel® Pentium® class microprocessors. Chipset 430 may interface with mass storage devices such as fixed media 444 or removable media 448 via PCI bus 446, or, alternately, via USB 442, an integrated controller electronics (IDE) bus (not shown), a small computer systems interconnect (SCSI) bus (not shown), or any other I/O busses. The fixed media 444 or removable media 448 may be magnetic disks, magnetic tape, magnetic diskettes, magneto-optical drives, CD-ROM, DVD-ROM, Flash memory cards, or many other forms of mass storage.

In the FIG. 4A embodiment, the four processors CPU A 410, CPU B 414, CPU C 418, and CPU D 422 are shown as four separate hardware entities. In other embodiments, the number of processors may differ. Indeed, the physically discrete processors may be replaced by separate hardware execution threads running on one or more physical processors. In the latter case these threads possess many of the attributes of additional physical processors. In order to have a generic expression to discuss using any mixture of multiple physical processors and multiple threads upon processors, the expression "logical processor" may be used to describe either a physical processor or a thread operating in one or more physical processors. Thus, one single-threaded processor may be considered a logical processor, and multi-threaded or multi-core processors may be considered multiple logical processors.

In one embodiment, chipset 430 interfaces with a modified LPC bus 450. Modified LPC bus 450 may be used to connect chipset 430 with a security token 454. Token 454 may in one embodiment include the TPM 471 envisioned by the Trusted Computing Platform Alliance (TCPA).

Figure 4B:
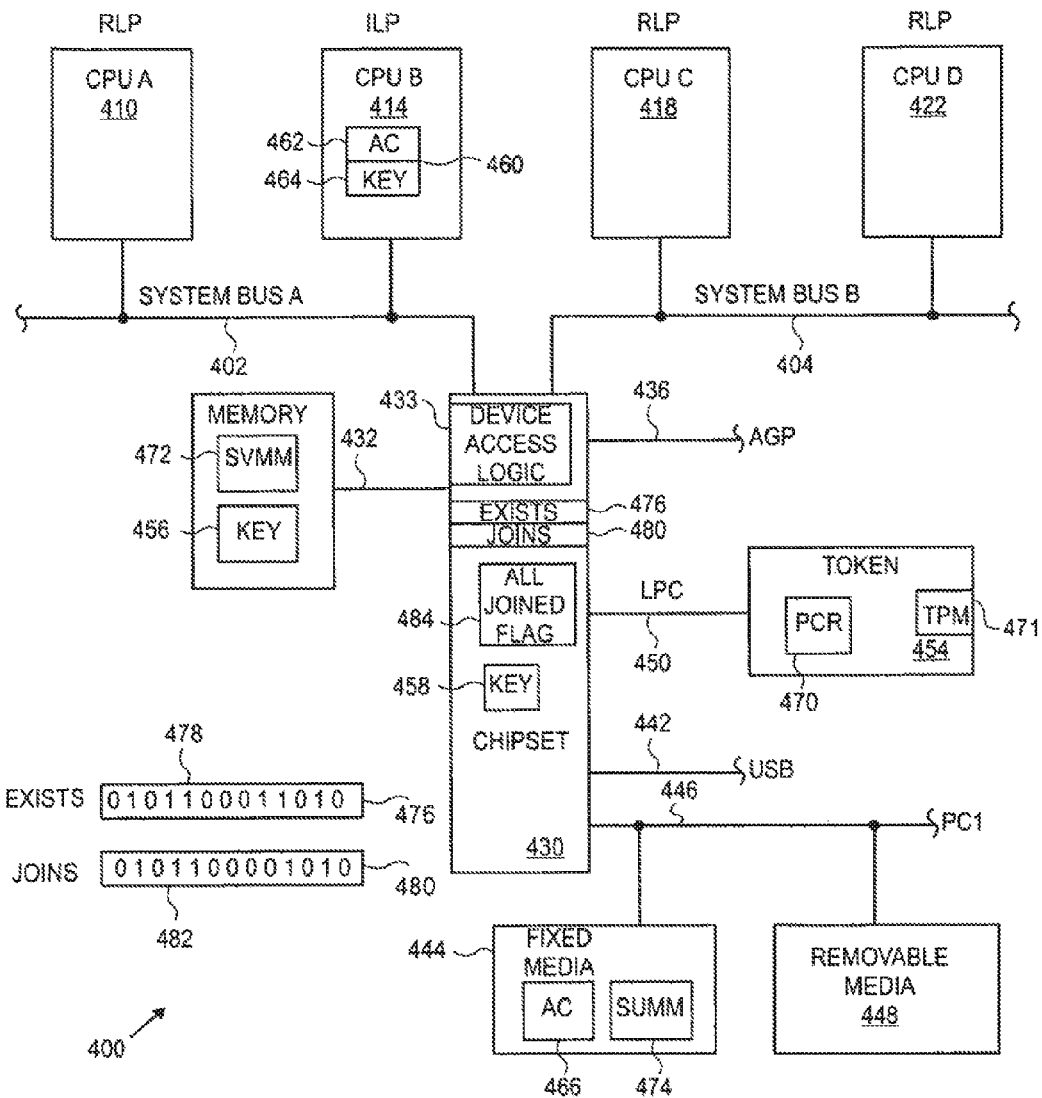
FIG. 4B is a schematic diagram of an exemplary microprocessor system adapted to support the secured software environment of FIG. 3, according to an alternate embodiment of the present invention.

Referring now to FIG. 4B, an alternate embodiment of a microprocessor system 490 adapted to support the secured software environment of FIG. 3 is shown. Differing from the FIG. 4A embodiment, CPU A 410 and CPU B 414 may be connected to chipset 428 with system bus A 402 whereas CPU C 418 and CPU D 422 may be connected to chipset 428 with system bus B 404. In other embodiments more than two system busses may be utilized. In another alternative embodiment, point-to-point busses may be used. Special instructions may support the issuance of special bus messages on system bus A 402 and system bus B 404 that may enable the proper synchronization of the processors while launching the secure environment. In one embodiment, the issuance of special bus messages may be supported by circuitry such as the bus message logic 206 of FIG. 2.

In one embodiment, chipset 428 is responsible for maintaining consistency and coherency across system bus A 402 and system bus B 404. If a bus message, standard or special, is sent across system bus A 402, chipset 428 reflects that message (when appropriate) onto system bus B 404, and vice-versa.

In an alternate embodiment, chipset 428 treats system bus A 402 and system bus B 404 as independent subsystems. Any special bus messages issued on system bus A 402 apply only to processors on that bus: similarly, special bus messages issued on system bus B 404 apply only to processors on that bus. Any protected memory that is established with respect to system bus A 402 is only accessible to processors connected to system bus A 402, and the processors on system bus B 404 may be treated as untrusted devices. To gain access to any protected memory established for CPU A 410 and CPU B 414 on system bus A 402, processors CPU C 418 and CPU D 422 on system bus B 404 must perform their own SENTER process, creating a registered environment equal to that created for the processors on system bus A 402.

Figure 5:
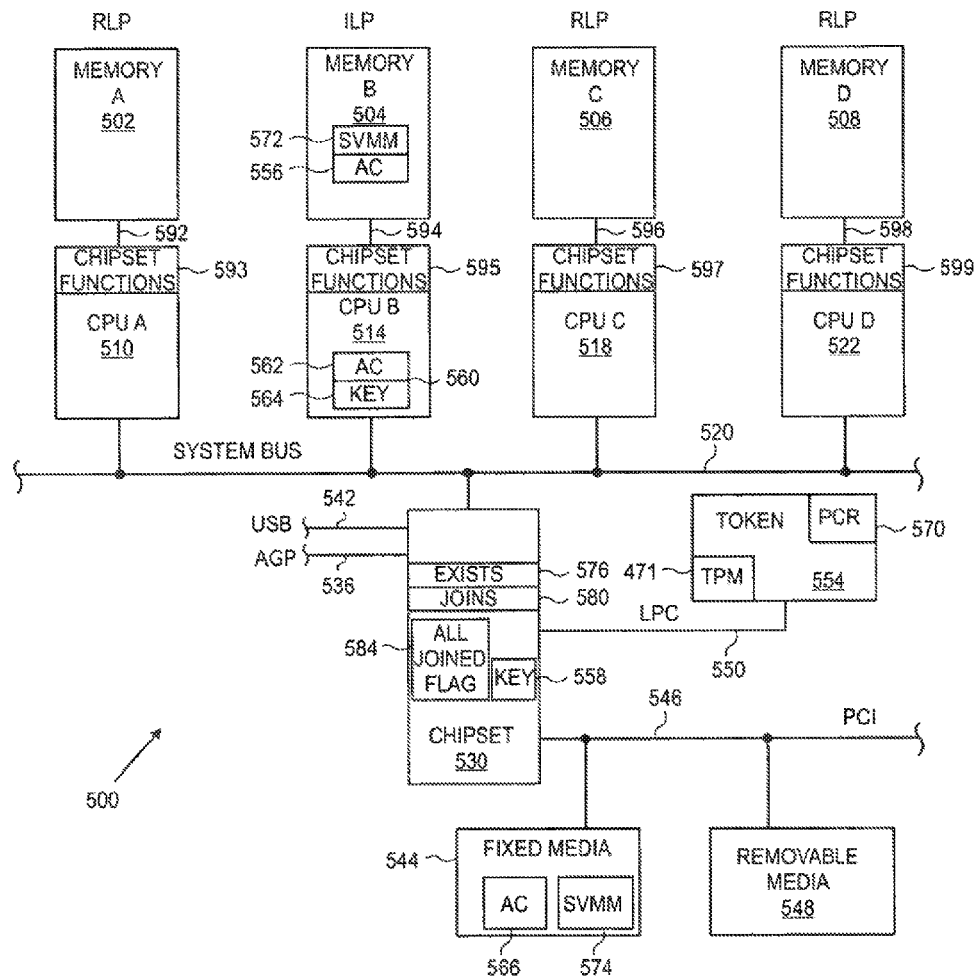
FIG. 5 is a schematic diagram of an exemplary microprocessor system adapted to support the secured software environment of FIG. 3, according to an alternate embodiment of the present invention.

Referring now to FIG. 5, a schematic diagram of an exemplary microprocessor system 500 adapted to support the secured software environment of FIG. 3 is shown, according to an alternate embodiment of the present invention. Differing from the FIG. 4A embodiment, each processor (for example, CPU A 510) may include certain chipset functions (for example, chipset functions 593) that, for example, perform memory controller functions and device access logic functions. These chipset functions thereby allow the direct connection of memory (for example, memory A 502) to the processor. Other chipset functions may remain in a separate chipset 530. Special bus messages may be issued across system bus 520.

Each processor may make indirect accesses to memory connected to other processors: however, these accesses may be considerably slower when compared to accesses to a processor's own memory. Prior to the start of the SENTER process, software may move copies of SINIT-AC 566 and SVMM 574 from fixed media 544 into local memory 504, forming copy of SINIT-AC 556 and copy of SVMM 572. In one embodiment, the memory 504 may be selected because it is directly accessed by the processor intended to be the ILP, in the FIG. 5 example this is CPU B 514. Alternatively, the SINIT-AC 566 and SVMM 574 copies may be placed in other memories attached to other (non-ILP) processors, so long as the ILP 514 has the ability to access those memories. CPU B ILP 514 begins the secure enter process by issuing the SENTER instruction, as already described in FIG. 2, and with similar consequences and bus cycles issued. Chipset 530 may utilize EXISTS register 576, JOINS register 580, and ALL_JOINED flag 584 as described above in connection with FIG. 2 to determine whether all processors have properly responded to the SENTER BUS MESSAGE and signal this information to the ILP. The ILP (CPU B 514) may again move the memory-resident copy of SINIT-AC 556 into secure memory 560, along with a copy of a public key 564. Upon verification and registration of SINIT-AC 556, ILP may then continue to verification and registration of the memory-resident copy of SVMM 572.

Figure 6:
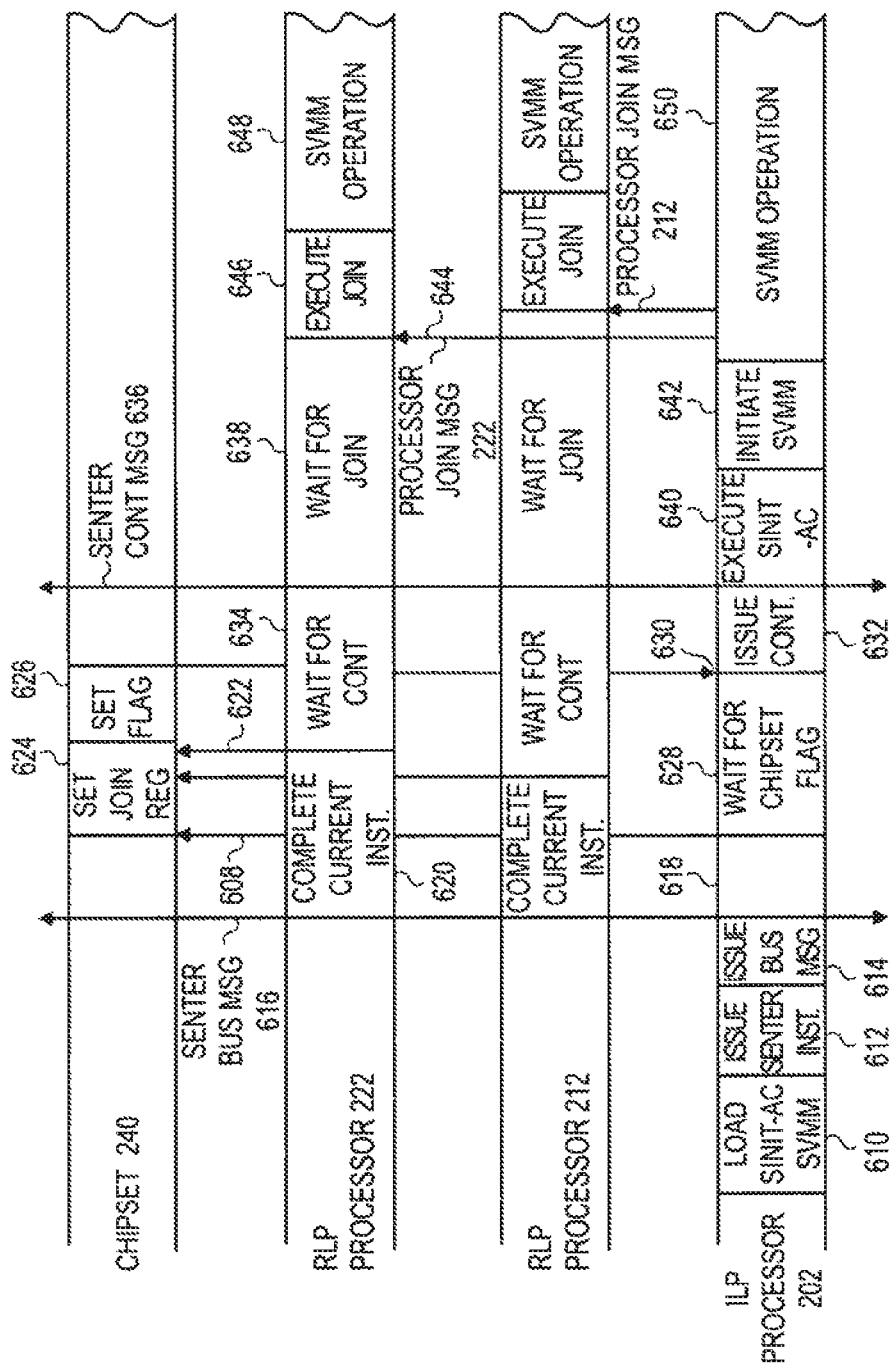
FIG. 6 is a time line drawing of the execution of software components, according to one embodiment of the present invention.

Referring now to FIG. 6, a time line drawing of various operations is shown, according to one embodiment of the present invention. The timeline of FIG. 6 shows the overall schedule of the operations discussed in connection with the exemplary system discussed in connection with FIG. 2 above. When software decides that secure or trusted operations are desired, at time 610 any software locates and makes a copy of SINIT-AC 280 and SVMM 282 available to a subsequent SENTER instruction. In this example, software loads a copy of SINIT-AC 280 and a copy of SVMM 282 into one or more memory pages 250-262. One processor, in the present example processor 202, is then selected to be the ILP, which issues the SENTER instruction at time 612. At time 614 the ILP's SENTER instruction issues the SENTER BUS MESSAGE 616. The ILP then issues its own SENTER ACK 608 at time 618 prior to entering a wait-for-chipset-flag state at time 628.

Each RLP, such as processor 222, respond to the SENTER BUS MESSAGE 616 by completing the current instruction during time 620. The RLP then issues its SENTER ACK 622 and then enters a state 634 where it waits for an SENTER CONTINUE MESSAGE.

The chipset 240 spends time 624 setting the JOINS register 272 responsive to the SENTER ACK messages observed on system bus 230. When the JOINS register 272 contents matches the EXISTS register 270 contents, chipset 240 sets the ALL_JOINED flag 246 at time 626.

During this time, the ILP may remain in a loop while polling the ALL_JOINED flag 246. When the ALL_JOINED flag 246 is set, and ILP determines that the ALL_JOINED flag 246 is set at time 630, the ILP may then issue the SENTER CONTINUE MESSAGE during time 632. When the SENTER CONTINUE MESSAGE is broadcast on system bus 230 at time 636, the RLPs may enter a wait-for-join state. For example, the RLP of processor 222 enters a wait-for-join state during time period 638.

Upon issuing the SENTER CONTINUE MESSAGE, the ILP may then (in time period 640) bring the public key of key register 244 of chipset 240 and a copy of SINIT-AC into its secure memory 208 to form a copy of the key and a copy of SINIT-AC. In another embodiment, key register 244 may contain a digest of the public key, and the actual public key may be included in, or with, the SINIT-AC. Upon authenticating the copy of SINIT-AC as described above in connection with FIG. 2, the ILP may then actually execute the copy of SINIT-AC within secure memory 208.

After the copy of SINIT-AC within secure memory 208 begins execution, it then (during time period 640) validates and registers the memory-resident copy of SVMM. After the copy of SVMM is registered in the PCR 278 of security token 276, the memory-resident copy of SVMM itself begins execution. At this time, during ongoing time period 650, SVMM operations are established in the ILP.

Among the first things that the ILP SVMM operation does is issue individual RLP JOIN MESSAGES on the system bus 230. An example is a processor 222 JOIN MESSAGE 644. This message may include a location in memory at which the RLP processor 222 may join in execution of the registered memory-resident copy of SVMM. Alternatively, the ILP SVMM operations may have registered a memory location in a predetermined location in the chipset or memory, and upon receiving the JOIN MESSAGE the RLP retrieves its starting address from this location. After receiving the processor 222 JOIN MESSAGE, and determining its starting address, during time period 646 the RLP processor 222 jumps to this location and joins execution of the registered memory-resident copy of the SVMM.

After all the RLPs have joined the registered memory-resident copy of the SVMM, secured operations are established throughout the microcomputer system 200.

Figure 7:
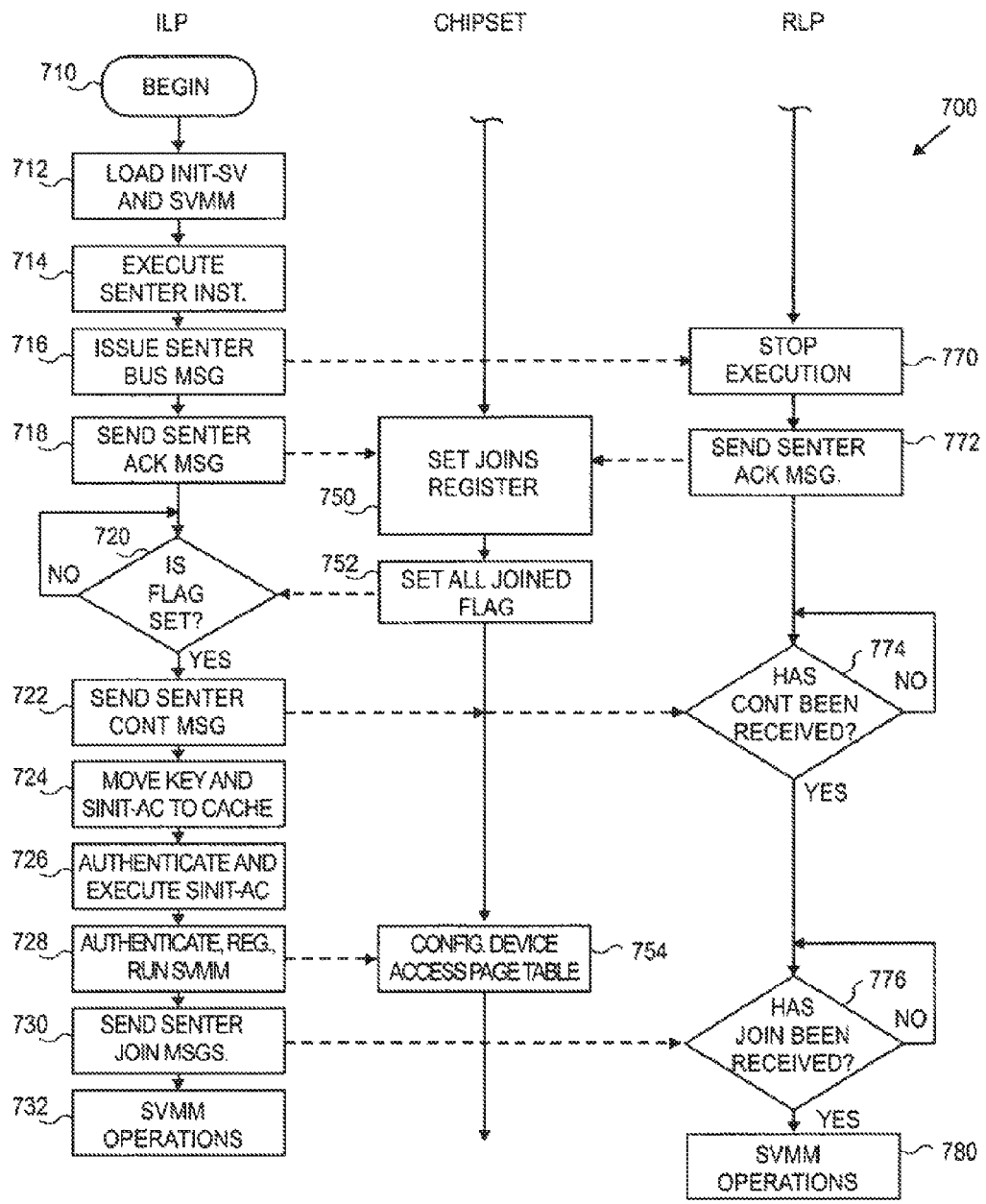
FIG. 7 is a flowchart of software and other process blocks, according to one embodiment of the present invention.

Referring now to FIG. 7, a flowchart of software and other process blocks is shown, according to one embodiment of the present invention. For the sake of clarity FIG. 7 only shows process blocks for a single representative RLP. In other embodiments there may be several responding logical processors.

The process 700 begins at block 710 when a logical processor makes a copy of the SINIT-AC and SVMM modules available for access by a subsequent SENTER instruction. In this example, in block 712 the ILP loads the SINIT-AC and SVMM code from mass storage into physical memory. In alternative embodiments, any logical processor may do so, not just the ILP. A processor becomes the ILP by executing the SENTER instruction, as identified in block 714. In block 716, the ILP SENTER instruction issues an SENTER BUS MESSAGE in block 716. The ILP then, in block 718, issues its own SENTER ACK message to the chipset. The ILP then enters a wait state, shown as decision block 720, and waits for the chipset to set its ALL_JOINED flag.

After each RLP receives the SENTER BUS MESSAGE in block 770, it halts execution with the end of the current instruction, and then in block 772 issues its own SENTER ACK. Each RLP then enters a wait state, shown as decision block 774, and waits for a SENTER CONTINUE MESSAGE to arrive from the ILP.

The chipset sets the corresponding bits in the JOINS register when SENTER ACK messages are received. When the JOINS register contents equals the EXISTS register contents, the chipset sets its ALL_JOINED flag, signaling the ILP to proceed from decision block 720.

The ILP, upon exiting decision block 720 on the YES path, then issues a SENTER CONTINUE MESSAGE in block 722. This signals each RLP to proceed from decision block 774. Each RLP then enters a second wait state, shown as decision block 776, and waits for a SENTER JOIN MESSAGE.

Meanwhile the ILP, in block 724, moves the public key of the chipset and the memory-resident copy of SINIT-AC into its own secure memory for secure execution. The ILP, in block 726, uses the key to validate the secure-memory-resident copy of SINIT-AC, and then executes it. The execution of SINIT-AC may perform tests of the system configuration and the SVMM copy, then registers the SVMM identity, and finally begins the execution of SVMM in block 728. As part of actions performed in block 728, the ILP SINIT code may configure device-access page table 248 and device-access logic 247 of memory and chipset to protect those memory pages used by the memory-resident copy of SVMM 282 from interference by non-processor devices, as shown in block 754.

After the ILP begins execution under the control of SVMM, in block 730 the ILP sends an individual SENTER JOIN MESSAGE to each RLP. After issuing the SENTER JOIN MESSAGE, the ILP then in block 732 begins SVMM operations.

The receipt of the SENTER JOIN MESSAGE causes each RLP to leave the wait state represented by decision block 776 along the YES path, and begin SVMM operations in block 780. The SENTER JOIN MESSAGE may contain the SVMM entry point the RLP branch to when joining SVMM operations. Alternatively, the ILP SVMM code may register the appropriate RLP entry point in a system location (for example, in the chipset), to be retrieved by the RLP upon receipt of the SENTER JOIN MESSAGE.

While various embodiments disclosed include two or more processors (either logical or physical processors), it should be understood that such multi-processor and/or multi-threaded systems are described in more detail to explain the added complexity associated with securing a system with multiple logical or physical processors. An embodiment also likely to be advantageous in less complex system may use only one processor. In some cases, the one physical processor may be multi-threading and therefore may include multiple logical processors (and accordingly have an ILP and an RLP as described). In other cases, however, a single-processor, single-threaded system may be used, and still utilize disclosed secure processing techniques. In such cases, there may be no RLP; however, the secure processing techniques still operate to reduce the likelihood that data can be stolen or manipulated in an unauthorized manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

The invention claimed is:

1. A system on a chip (SoC) comprising:
   a processor including:
      a trusted memory of the processor to support secure initialization operations,
      secure initialization logic of the processor to establish a root of trust for a secure execution environment,
      execution logic of the processor to execute secure initialization program code within the secure execution environment, at least a portion of the secure initialization program code to be copied into the trusted memory,
      the execution logic to validate the secure initialization program code prior to execution,
      the execution logic to validate a virtual machine monitor (VMM) and copy the VMM to a trusted system memory area within the secure execution environment, and
      wherein the execution logic includes one or more cores to execute one or more threads; and
   a memory controller to couple the processor to a system memory;
the processor and the memory controller on a single semiconductor die.

2. The SoC of claim 1, further comprising access logic to permit or deny access to memory pages within the system memory, the access logic on the single semiconductor die.

3. The SoC of claim 1, wherein validation of the VMM by the execution unit is to include cryptographic authentication of the VMM.

4. A system on a chip (SoC) comprising:
   a processor including:
      a trusted memory of the processor to support secure initialization operations,
      execution logic of the processor, the execution logic including secure initialization logic to establish a root of trust for a secure execution environment, the execution logic to execute secure initialization program code within the secure execution environment, at least a portion of the secure initialization program code to be copied into the trusted memory, the execution logic to validate the secure initialization program code prior to execution, the execution logic to validate a virtual machine monitor (VMM) and copy the VMM to a trusted system memory area within the secure execution environment, and wherein the execution logic includes one or more cores to execute one or more threads; and a memory controller to couple the processor to a system memory;

the processor and the memory controller on a single semiconductor die.

5. The SoC of claim 4, further comprising access logic to permit or deny access to memory pages within the system memory, the access logic on the single semiconductor die.

6. The SoC of claim 4, wherein validation of the VMM by the execution unit is to include cryptographic authentication of the VMM.

* * * * *